(12) United States Patent
Sakurai et al.

(10) Patent No.: US 12,122,736 B2
(45) Date of Patent: Oct. 22, 2024

(54) SALTY TASTE-ENHANCING AGENT AND MANUFACTURING METHOD THEREFOR, AND SALTY TASTE-ENHANCING METHOD

(71) Applicant: NISSIN FOODS HOLDINGS CO., LTD., Osaka (JP)

(72) Inventors: Takanobu Sakurai, Osaka (JP); Yoichi Kasahara, Osaka (JP); Mitsuru Tanaka, Osaka (JP); Keiko Abe, Saitama (JP); Tomiko Asakura, Tokyo (JP); Haruyuki Yamashita, Saitama (JP)

(73) Assignee: Nissan Foods Holdings Co., LTD., Osaka (JP)

( * ) Notice: Subject to any disclaimer, the term of this patent is extended or adjusted under 35 U.S.C. 154(b) by 306 days.

(21) Appl. No.: 14/436,449

(22) PCT Filed: Oct. 17, 2013

(86) PCT No.: PCT/JP2013/078178
§ 371 (c)(1),
(2) Date: Apr. 16, 2015

(87) PCT Pub. No.: WO2014/061734
PCT Pub. Date: Apr. 24, 2014

(65) Prior Publication Data
US 2015/0250217 A1     Sep. 10, 2015

(30) Foreign Application Priority Data

Oct. 18, 2012  (JP) ................. 2012-230673

(51) Int. Cl.
| | | |
|---|---|---|
| *C07C 277/08* | (2006.01) | |
| *A23L 2/56* | (2006.01) | |
| *A23L 27/00* | (2016.01) | |
| *A23L 27/20* | (2016.01) | |
| *A23L 27/40* | (2016.01) | |
| *C07C 279/02* | (2006.01) | |
| *C07C 279/04* | (2006.01) | |
| *C07C 279/08* | (2006.01) | |
| *C07C 279/14* | (2006.01) | |
| *C07C 319/14* | (2006.01) | |
| *C07C 323/44* | (2006.01) | |
| *C07C 323/45* | (2006.01) | |

(52) U.S. Cl.
CPC ............. *C07C 277/08* (2013.01); *A23L 2/56* (2013.01); *A23L 27/202* (2016.08); *A23L 27/2056* (2016.08); *A23L 27/40* (2016.08); *A23L 27/45* (2016.08); *A23L 27/88* (2016.08); *C07C 279/02* (2013.01); *C07C 279/04* (2013.01); *C07C 279/08* (2013.01); *C07C 279/14* (2013.01); *C07C 319/14* (2013.01); *C07C 323/44* (2013.01); *C07C 323/45* (2013.01); *A23V 2002/00* (2013.01)

(58) Field of Classification Search
CPC ... C07C 277/08; C07C 279/02; C07C 279/04; C07C 279/08; C07C 279/14; C07C 319/14; C07C 323/44; C07C 323/45; A23L 27/88; A23L 27/2056; A23L 27/40; A23L 27/45; A23L 27/202; A23L 2/56; A23V 2002/00
USPC ........................................ 426/535, 534, 650
See application file for complete search history.

(56) References Cited

U.S. PATENT DOCUMENTS

| | | |
|---|---|---|
| 5,723,133 A | 3/1998 | Nagai et al. |
| 5,900,435 A | 5/1999 | Meglasson |
| 5,939,078 A | 8/1999 | Fujimura et al. |

FOREIGN PATENT DOCUMENTS

| | | |
|---|---|---|
| GB | 1272499 A | 4/1917 |
| JP | S58-10555 A | 1/1983 |
| JP | 63287460 | 11/1988 |
| JP | 6510286 | 11/1994 |
| JP | 753542 | 2/1995 |
| JP | H09-202710 A | 8/1997 |
| JP | 2010-506929 A | 3/2010 |
| JP | H753542 | 2/2019 |
| JP | S63287460 | 2/2020 |
| WO | 2008020568 | 2/2008 |
| WO | 2008/051447 A2 | 5/2008 |
| WO | WO 2011/097344 A1 | 8/2011 |
| WO | WO 2012/085815 A1 | 6/2012 |

OTHER PUBLICATIONS

Short, James H. et al., "Sympathetic Nervous System Blocking Agents, Derivatives of Guanidine and Related Compounds", Journal of Medicinal Chemistry, vol. 6, 1963, pp. 275-283.
Ludwig et al., "Synthesis and Hipoglycemic Activity of Substituted Alkyl- and Alkoxyguanidines", Journal of Medicinal Chemistry, vol. 13, 1970, pp. 60-63.
Mourgue et al., The Preparation of Alpha.-Guanidino Acids and of Amino and Amino Alcohol Derivatives of Guanidine, Bulletin De La Societe Chimique De France, 1948, pp. 182-183.
Kawai et al., Synthesis of Beta.,.Gamma.-Dihydroxypropylguanidine, Bulletin of the Chemical Society of Japan, vol. 11, No. 3, 1936, pp. 141-143.

(Continued)

*Primary Examiner* — Jeffrey P Mornhinweg
(74) *Attorney, Agent, or Firm* — Maynard Nexsen PC; Todd A. Serbin

(57) ABSTRACT

An object of the present invention is to provide a novel salty taste-enhancing agent and production method therefor, and salty taste-enhancing method for a food and beverage. As means for achieving such object, provided is a salty taste-enhancing agent.

4 Claims, No Drawings

(56) References Cited

OTHER PUBLICATIONS

Brand et al., AGFD 261—Slaty Taste Amplification: Effects of Amino Acids and Guanidinium-Containing Compounds, American Chemical Society. Abstracts of Papers, col. 236, 2008, p. AGFD 261.
Fitz, Wolfgang; Extended European Search Report; EP 13846315; Apr. 26, 2016.
Kato, Tadashi, "Occurence of Guanidino Compounds in Several Plants", National Grassland Research Institute, Oct. 31, 1986, pp. 487-491, vol. 32, No. 3, Soil Science and Nutrition, Japan.
Irreverre, F., "Occurence of Gamma-Guanidinobutyric Acid", National Institute of Arthritis and Metabolic Diseases, Oct. 5, 1957, pp. 704-705, vol. 180, No. 4588, Nature Publishing Group.
Kato, Tadashi, "Occurence of Guanidino Compounds in Several Plants", National Grassland Research Institute, Oct. 31, 1983, pp. 487-491, vol. 32, No. 3, Soil Science and Nutrition, Japan.
Patlak, Margie, et al., "The Flavor of Health", Fall 2008, 16 pages, The Monnell Connection, Online.
Brand, Joseph, et al., "Salty taste amplification: Effects of amino acids and guanidinium-containing compounds", Agricultural & Food Chemistry, Aug. 17-21, 2008, 1 page, Abstract of the 236th ACS National Meeting, Philadelphia, PA.
Fitz, Wolfgang; EP13846315.3-1451; Communication pursuant to Article 94(3) EPC; 5 pages; Apr. 21, 2017.
Kitada, Yusuke; Notification of Reasons for Refusal for the corresponding JP Patent Application No. 2014-542170, Jul. 4, 2017. (English translation included).
Fishbein et al., "Some New 1-(Nitroxyalkyl)-3-nitroguanidines and their Cyclic Products", Journal of American Chemical Society, Jan. 18, 1954, pp. 3217-3219, vol. 76, No. 12, Indian Head, Maryland.

SALTY TASTE-ENHANCING AGENT AND MANUFACTURING METHOD THEREFOR, AND SALTY TASTE-ENHANCING METHOD

TECHNICAL FIELD

Cross-Reference to Related Application

This application claims priority from Japanese Patent Application No. 2012-230673, filed on Oct. 18, 2012, the entire disclosure of which is incorporated herein by reference.

The present invention mainly relates to a novel salty taste-enhancing agent and production method therefor, and salty taste-enhancing method for a food and beverage. The present invention also relates to a food additive, a seasoning, and a food and beverage.

BACKGROUND ART

Sodium is an essential mineral for a living organism, and salt (sodium chloride) is an extremely important substance as a source of sodium intake. A sodium ion contributes to, for example, maintenance of an extracellular fluid volume, regulation of osmotic pressure and acid-base equilibrium, neurotransmission, and formation of a membrane potential involved in transmembrane active transport of a substance, and thus is indispensable for life maintenance.

However, in order to improve food palatability, salt intake tends to become excessive. For example, goal salt intakes proposed by the Ministry of Health, Labour and Welfare, Japan are less than 9.0 g per day for adult human males and less than 7.5 g per day for adult human females ("Dietary Reference Intakes for Japanese (2010 edition)" (Ministry of Health, Labour and Welfare)). In addition, a goal salt intake proposed by the World Health Organization (WHO) is less than 6.0 g per day ("Dietary Reference Intakes for Japanese (2010 edition)" (Ministry of Health, Labour and Welfare)) On the other hand, actual salt intakes for Japanese are 11.6 g per day for adult human males and 9.9 g per day for adult human females. Thus, there are huge gaps between the actual intakes and the goal values ("National Health and Nutrition Survey, 2009" (Ministry of Health, Labour and Welfare)).

It has been pointed out that such excessive salt intake may serve as a cause for an increase in blood pressure, and it has been feared that the increase in blood pressure may cause cerebral stroke and heart diseases. Under such circumstances, there is a strong demand for a salt alternative or salty taste-enhancing agent, which, like salt, can impart a salty taste to a food, as one means for achieving a reduced salt intake.

The salt alternative refers to a material that may be used in place of salt and exhibits a salty taste by itself. As the salt alternative, potassium chloride is known (Patent Literature 1). However, potassium chloride exhibits a bitter taste in addition to the salty taste, and hence reduces food palatability. In addition, excessive potassium intake is physiologically inconvenient.

As the salty taste-enhancing agent, there is given an ingredient that has substantially no salty taste in itself but allows a salty taste of salt (sodium chloride) to be strongly sensed when used in combination with the salt. Various salty taste-enhancing agents have been proposed heretofore. Under the present circumstances, however, additional improvements have been demanded in terms of strength of a salty taste-enhancing effect.

CITATION LIST

Patent Literature

[PTL 1] JP 63-287460 A

SUMMARY OF INVENTION

Technical Problem

A main object of the present invention is to provide a novel salty taste-enhancing agent and salty taste-enhancing method for a food and beverage.

Solution to Problem

The inventors of the present invention have made extensive studies in order to achieve the above-mentioned object. As a result, the inventors have found that a compound represented by the following general formula (1) or a salt thereof may be suitably used as a salty taste-enhancing agent. The present invention has been completed through studies further made based on such finding.

That is, the present invention encompasses aspects of the invention according to the following items.

Item 1. A salty taste-enhancing agent, including a compound represented by the following general formula (1) or a salt thereof:

(1)

where R represents:
  (i) a linear or branched hydrocarbon group having 1 to 5 carbon atoms that may be interrupted by a heteroatom, in which the hydrocarbon group may have at least one group selected from the group consisting of a carboxyl group and a hydroxyl group; or
  (ii) a hydrogen atom.

Item 2. A salty taste-enhancing agent according to Item 1, in which the compound represented by the general formula (1) or the salt thereof includes a compound represented by any one of the following general formulae (2) to (6) or a salt thereof:

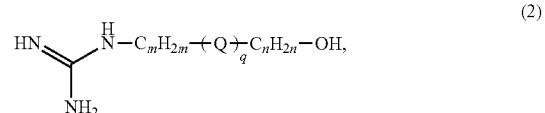

(2)

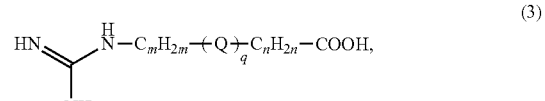

(3)

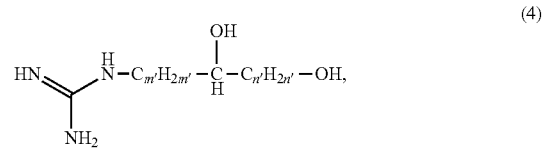

(4)

-continued

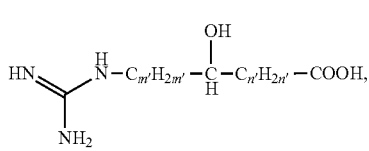
(5)

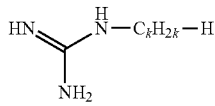
(6)

where:
Q represents a heteroatom, and q represents 0 or 1;
m and n each represent an integer of from 1 to 4, and m+n is an integer of from 3 to 5;
m' and n' each represent an integer of from 1 to 3, and m'+n' is an integer of from 2 to 4; and
k represents an integer of from 0 to 3.

Item 3. A salty taste-enhancing agent according to Item 1, in which the compound represented by the general formula (1) or the salt thereof includes a compound represented by the following general formula (7) or a salt thereof:

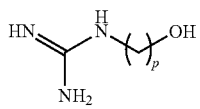
(7)

where p represents an integer of from 3 to 5.

Item 4. A production method for a salty taste-enhancing agent including a compound represented by the following general formula (1) or a salt thereof:

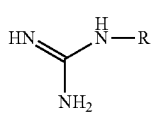
(1)

where R represents:
(i) a linear or branched hydrocarbon group having 1 to 5 carbon atoms that may be interrupted by a heteroatom, in which the hydrocarbon group may have at least one group selected from the group consisting of a carboxyl group and a hydroxyl group; or
(ii) a hydrogen atom,
the production method including a step of subjecting S-methylisothiourea or a salt thereof to a reaction with a primary amine compound represented by the following general formula (X):

$H_2N-R$ (X)

where R is as defined above.

Item 5. A production method for a salty taste-enhancing agent including a compound represented by any one of the following formulae (2) to (6) or a salt thereof:

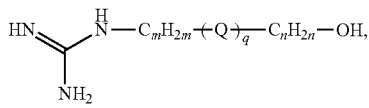
(2)

-continued

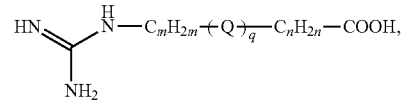
(3)

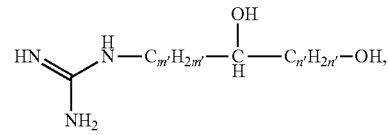
(4)

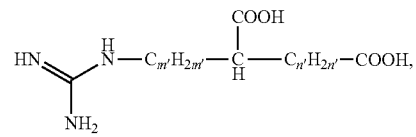
(5)

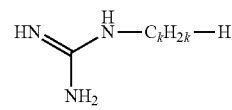
(6)

where:
Q represents a heteroatom, and q represents 0 or 1;
m and n each represent an integer of from 1 to 4, and m+n is an integer of from 3 to 5;
m' and n' each represent an integer of from 1 to 3, and m°+n' is an integer of from 2 to 4; and
k represents an integer of from 0 to 3,
the production method including a step of subjecting S-methylisothiourea or a salt thereof to a reaction with an aminoalcohol compound represented by the following general formula (X2) or (X4), an aminocarboxylic acid compound represented by the following general formula (X3) or (X5), or an alkylamine compound represented by the following general formula (X6):

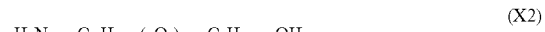
(X2)

(X3)

(X4)

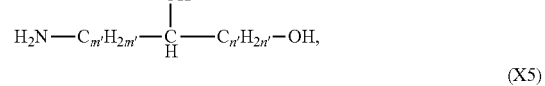
(X5)

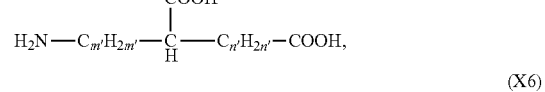
(X6)

where Q, q, m, n, m', n', and k are as defined above.

Item 6. A production method for a salty taste-enhancing agent including a compound represented by the following general formula (7) or a salt thereof:

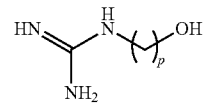
(7)

where p represents an integer of from 3 to 5,
the production method including a step of subjecting S-methylisothiourea or a salt thereof to a reaction with an aminoalcohol compound represented by the following general formula (X7):

(X7)

where p is as defined above.

Item 7. A food additive, including the compound or salt thereof as described in any one of Items 1 to 3.

Item 8. A seasoning, including the compound or salt thereof as described in any one of Items 1 to 3.

Item 9. A seasoning according to Item 5, further including sodium chloride.

Item 10. A food and beverage, including the compound or salt thereof as described in any one of Items 1 to 3.

Item 11. A food and beverage, including 10 ppm or more of the compound or salt thereof as described in any one of Items 1 to 3.

Item 12. A food and beverage according to Item 10 or 11, in which the food and beverage has added thereto the compound or salt thereof as described in any one of Items 1 to 3.

Item 13. A food and beverage according to any one of Items 10 to 12, further including sodium chloride.

Item 14. A salty taste-enhancing method for a food and beverage, including a step of adding the compound or salt thereof as described in any one of Items 1 to 3 to a food and beverage.

Advantageous Effects of Invention

According to one embodiment of the present invention, the novel salty taste-enhancing agent is provided. The salty taste-enhancing agent of the present invention has a high salty taste-enhancing effect and has no salty taste and no foreign taste and foreign odor other than the salty taste in itself. Therefore, for example, the addition of the salty taste-enhancing agent of the present invention as a food additive, a seasoning, or the like to salt can provide a food having a reduced salt content while having a salty taste with high palatability.

DESCRIPTION OF EMBODIMENTS

1. Salty Taste-Enhancing Agent

The present invention relates to a salty taste-enhancing agent. Herein, the salty taste-enhancing agent refers to a substance that has substantially no salty taste in itself but allows a salty taste of salt (sodium chloride) to be strongly sensed when used in combination with the salt. Specific examples thereof include: a substance having an effect of allowing a subthreshold salty taste of a salty taste substance, which has been unable to be sensed, to be sensed when allowed to coexist with the salty taste substance; and a substance having an effect of inducing a strong salty taste through its addition.

A salty taste-enhancing agent of the present invention includes a compound represented by the following general formula (1) or a salt thereof.

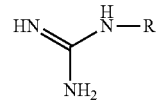
(1)

[In the formula, R represents:
(i) a linear or branched hydrocarbon group having 1 to 5 carbon atoms that may be interrupted by a heteroatom, in which the hydrocarbon group may have at least one group selected from the group consisting of a carboxyl group and a hydroxyl group; or
(ii) a hydrogen atom.]

The compound represented by the general formula (1) is a compound having a guanidino group, or guanidine.

The hydrocarbon group may be a saturated hydrocarbon group, or may be an unsaturated hydrocarbon group.

A specific example of the linear or branched hydrocarbon group having 1 to 5 carbon atoms in the case of not being interrupted by a heteroatom is an alkyl group such as a methyl group, an ethyl group, a n-propyl group, an isopropyl group, a n-butyl group, an isobutyl group, a sec-butyl group, a tert-butyl group, a n-pentyl group, an isopentyl(3-methylbutyl) group, a neo-pentyl(2,2-dimethylpropyl) group, a 1-methylbutyl group, a 2-methylbutyl group, a 1-ethylpropyl group, a 1,1-dimethylpropyl group, or a 1,2-dimethylpropyl group.

When the hydrocarbon group is interrupted by a heteroatom, there is given, for example, a hydrocarbon group having 2 to 5 carbon atoms in which a carbon skeleton of the alkyl group is interrupted by one or more, preferably one heteroatom.

Specific examples of the heteroatom include an oxygen atom and a sulfur atom. The heteroatom is preferably an oxygen atom.

The hydrocarbon group may have at least one group selected from the group consisting of a carboxyl group and a hydroxyl group. When the hydrocarbon group has two or more groups, the groups may be identical to or different from each other. Specific examples thereof include, but not limited to, aspects such as an aspect having one carboxyl group, an aspect having one hydroxyl group, an aspect having a total of two groups, i.e., one carboxyl group and one hydroxyl group, an aspect having two carboxyl groups, and an aspect having two hydroxyl groups. An aspect having one or two hydroxyl groups is given as a preferred aspect from the viewpoint that the salty taste-enhancing effect is particularly high.

When the compound represented by the general formula (1) has an asymmetric carbon atom, the compound may contain an R isomer, an S isomer, or a mixture thereof at any ratio, or may be a racemic mixture. The compound of the present invention, when having two or more asymmetric carbon atoms, may be any one of the isomers or a mixture thereof.

The salt of the compound is not particularly limited as long as the salt does not affect the salty taste-enhancing effect. In addition, it is preferred that the salt impart no foreign taste and foreign odor. Examples of such salt include salts of organic acids and salts of inorganic acids. Of those, inorganic acids are preferred, and a hydrochloride is particularly preferred.

A preferred aspect of the salty taste-enhancing agent of the present invention is exemplified by a salty taste-enhancing agent including a compound represented by any one of the following general formulae (2) to (6) or a salt thereof. The salty taste-enhancing agent including a compound represented by any one of the following general formulae (2) to (6) or a salt thereof is particularly preferred from the viewpoints that the salty taste-enhancing effect is high and very little or no foreign taste and foreign odor can be sensed.

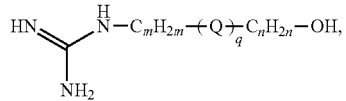
(2)

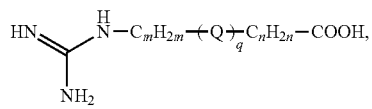
(3)

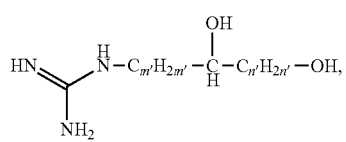
(4)

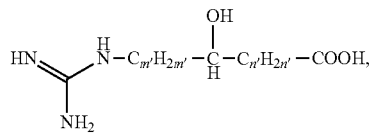
(5)

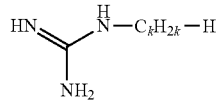
(6)

[In the formulae:
Q represents a heteroatom, and q represents 0 or 1;
m and n each represent an integer of from 1 to 4, and m+n is an integer of from 3 to 5;
m' and n' each represent an integer of from 1 to 3, and m'+n° is an integer of from 2 to 4; and
k represents an integer of from 0 to 3.]

In the general formulae (2) and (3), m and n each represent an integer of from 1 to 4, and m+n is an integer of from 3 to 5. In the general formulae (4) and (5), m' and n' each represent an integer of from 1 to 3, and m'+n' is an integer of from 2 to 4. In the general formula (6), k represents an integer of from 0 to 3.

In the general formulae (2) to (6), $—C_mH_{2m}—$, $—C_nH_{2n}—$, $—C_mH_{2m'}—$, $—C_nH_{2n'}—$, and $—C_kH_{2k}—$ represent alkylene groups having m, n, m', n', and k carbon atoms, respectively. Preferred aspects of the alkylene groups include the following linear alkylene groups or branched alkylene groups each having a methyl group as a branch, in such a range that m and n, m' and n', or k satisfies the above-mentioned condition.

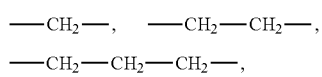

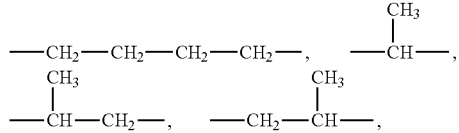

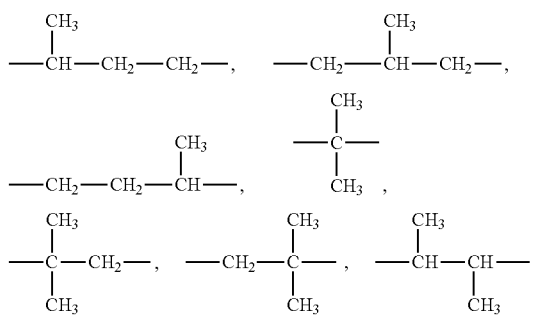

Particularly preferred aspects of the alkylene groups include the following linear alkylene groups.

$—CH_2—$, $—CH_2—CH_2—$, $—CH_2CH_2CH_2—$, $—CH_2CH_2CH_2CH_2—$

Specific examples of the compound represented by the general formula (2) are given below.

Cases where q represents 0:

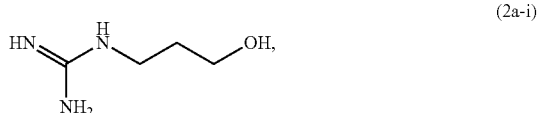
(2a-i)

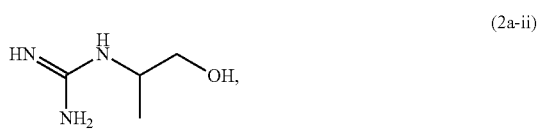
(2a-ii)

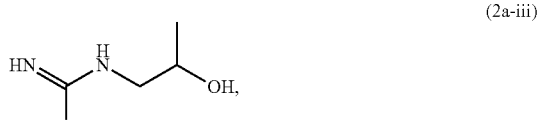
(2a-iii)

(2a-iv)

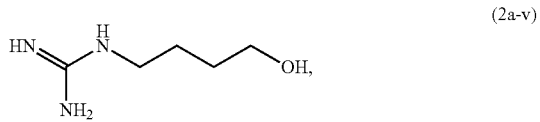
(2a-v)

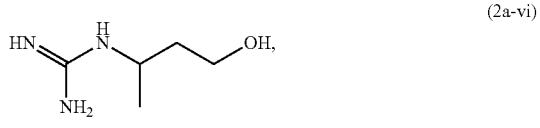
(2a-vi)

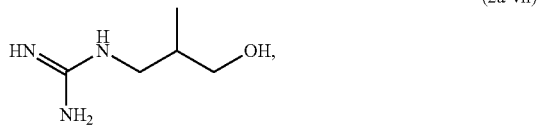
(2a-vii)

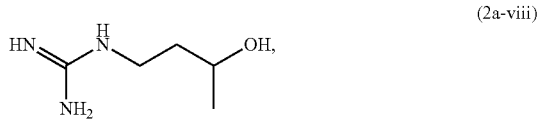
(2a-viii)

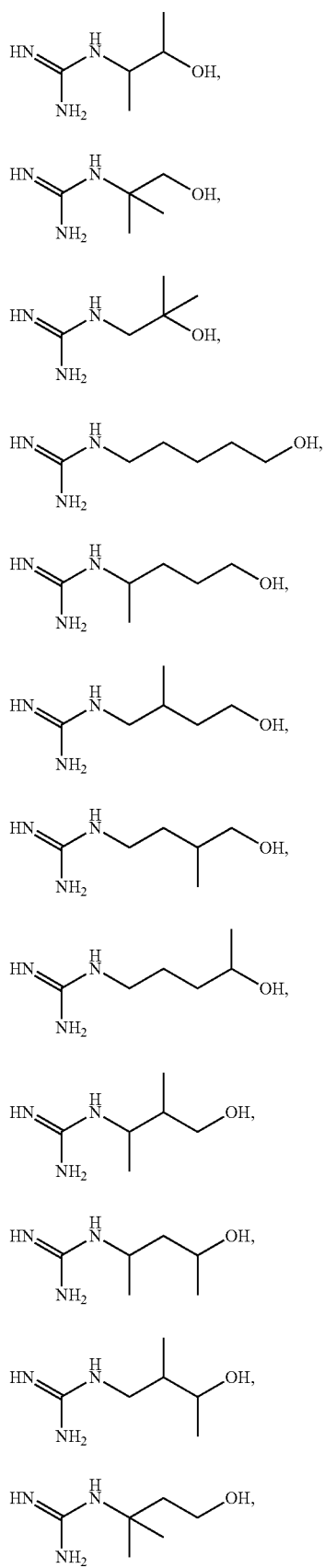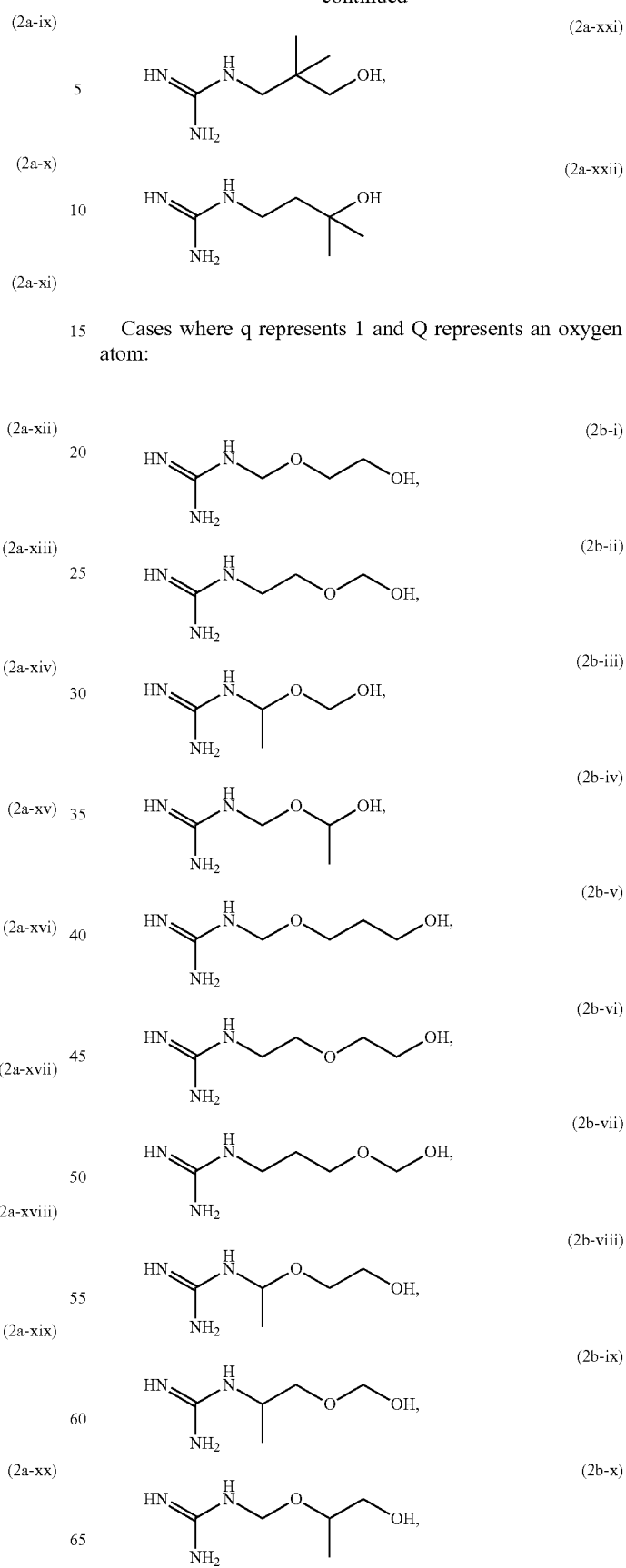
Cases where q represents 1 and Q represents an oxygen atom:

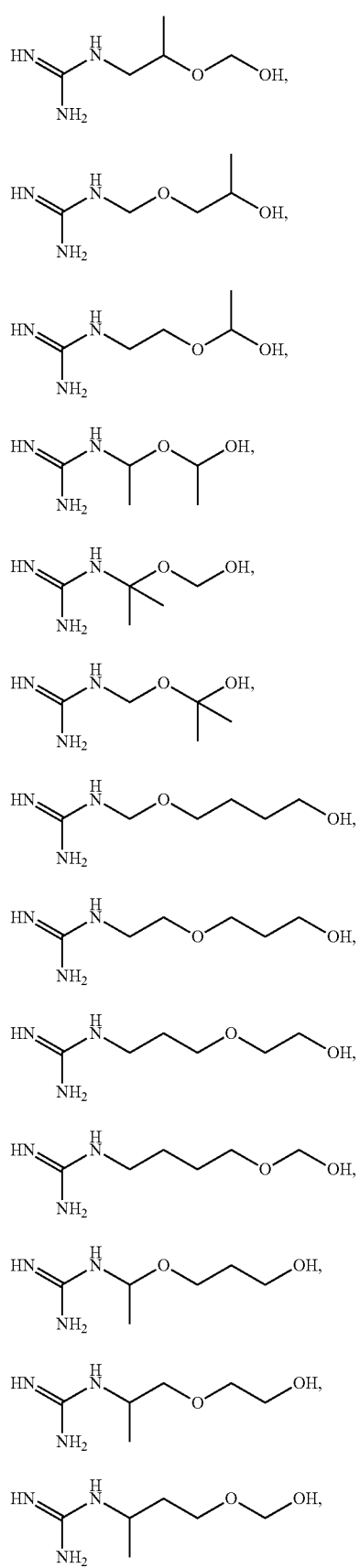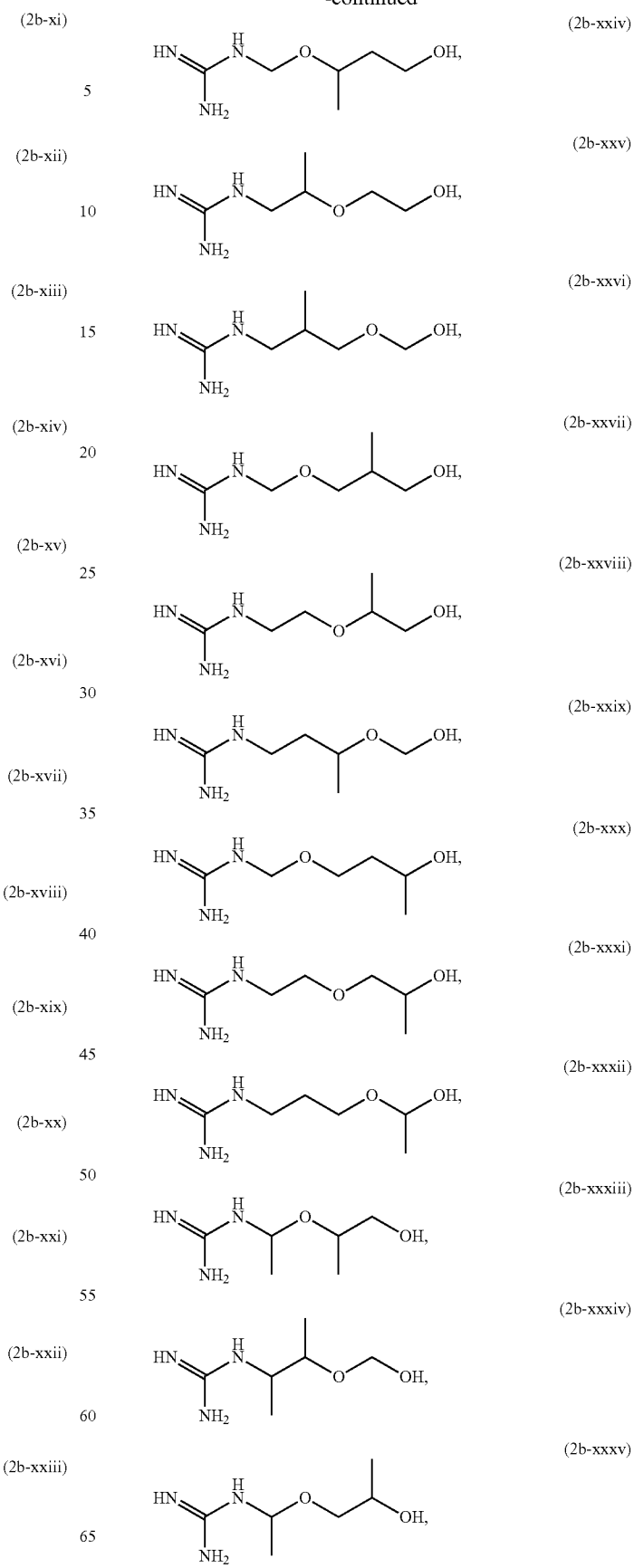

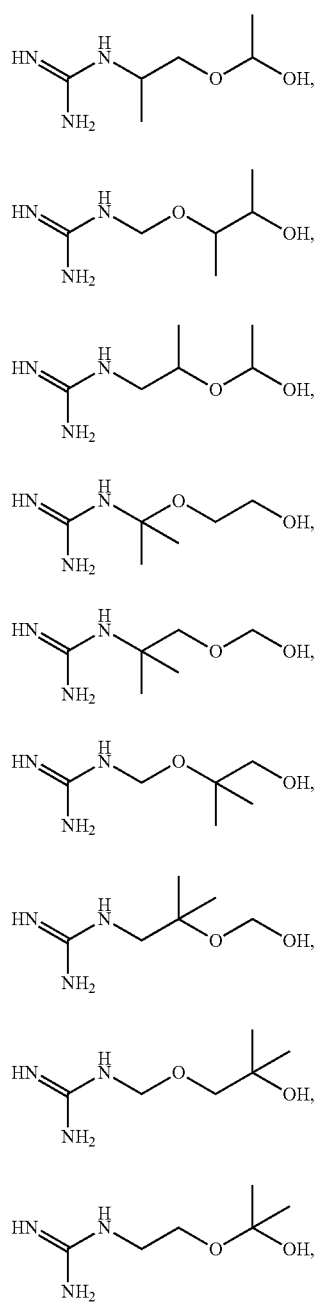
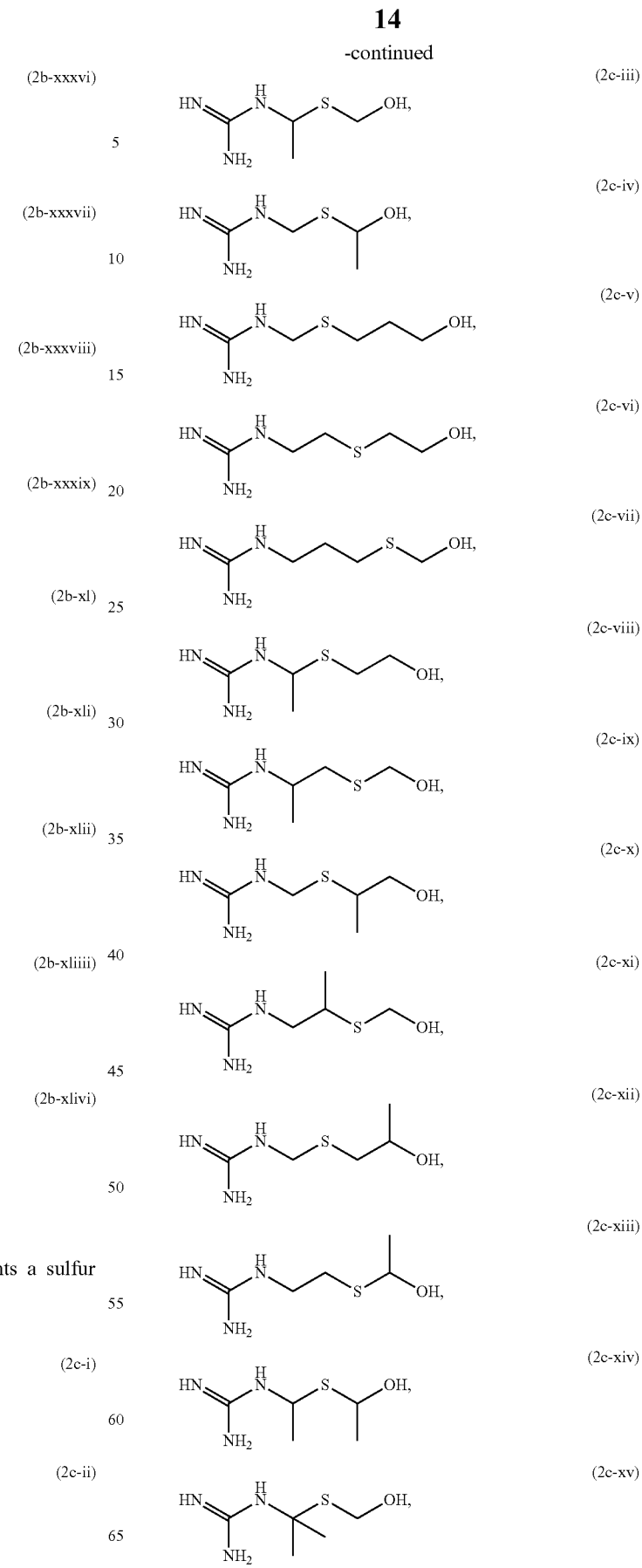
Cases where q represents 1 and Q represents a sulfur atom:

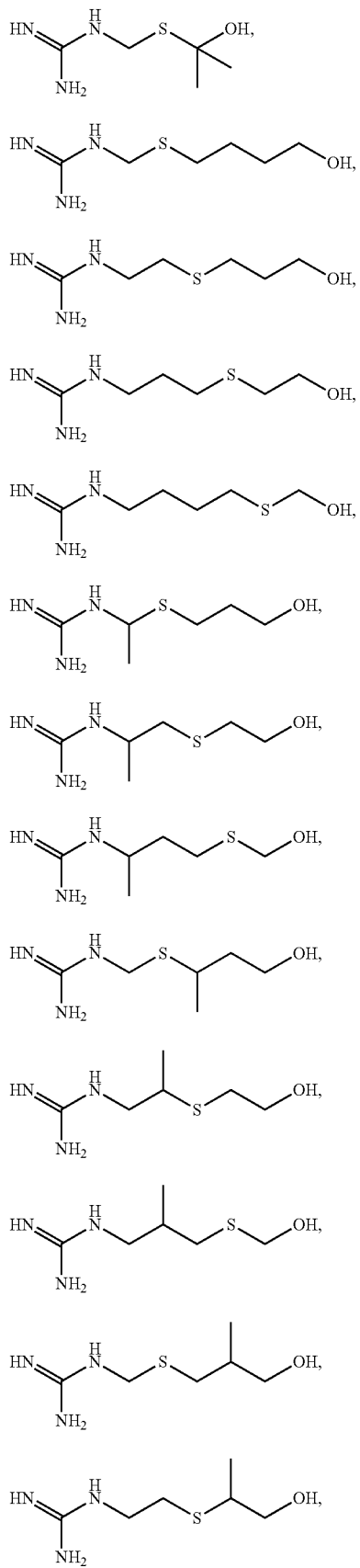
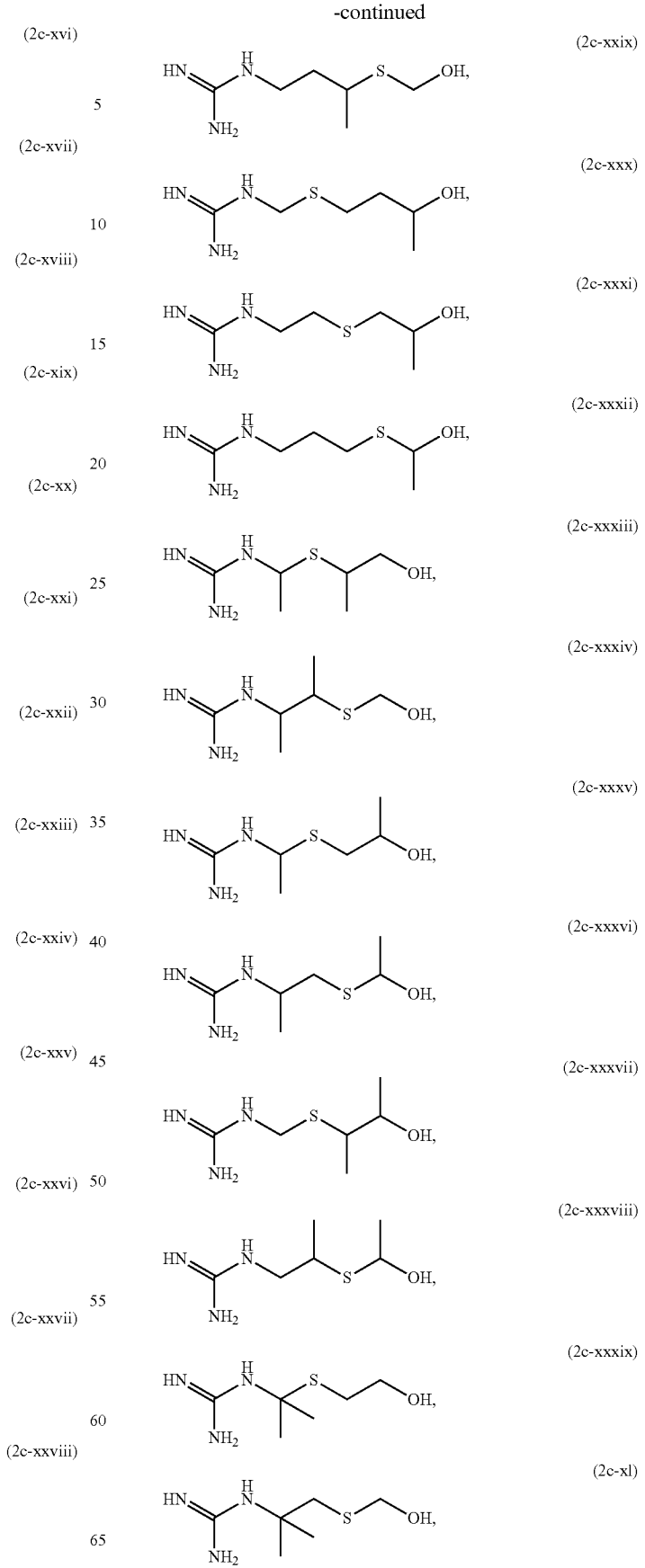

-continued
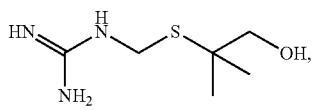 (2c-xli)
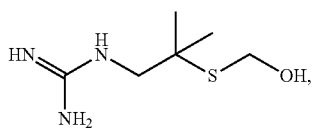 (2c-xlii)
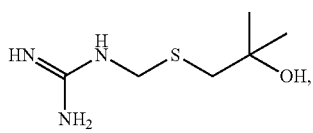 (2c-xliiii)
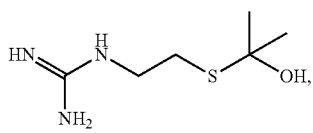 (2c-xlivi)
Specific examples of the compound represented by the general formula (3) are given below.
Cases where q represents 0:
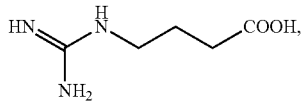 (3a-i)
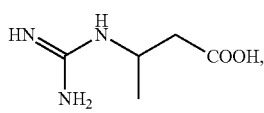 (3a-ii)
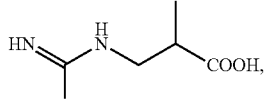 (3a-iii)
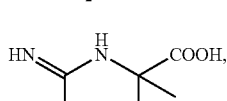 (3a-iv)
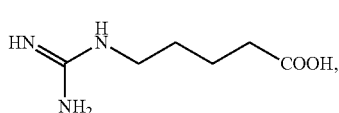 (3a-v)
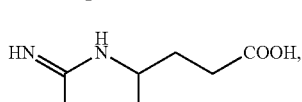 (3a-vi)
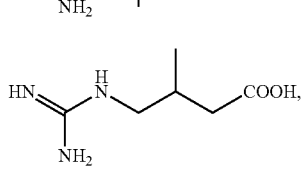 (3a-vii)
-continued
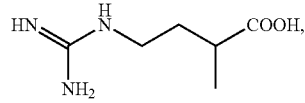 (3a-viii)
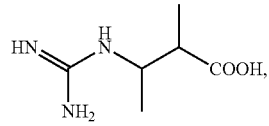 (3a-ix)
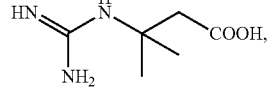 (3a-x)
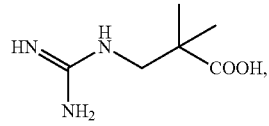 (3a-xi)
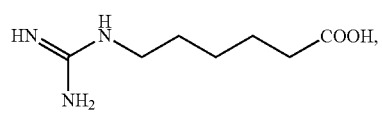 (3a-xii)
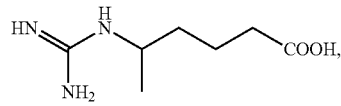 (3a-xiii)
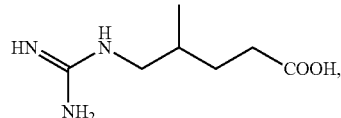 (3a-xiv)
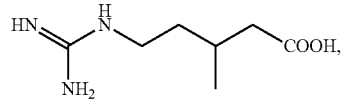 (3a-xv)
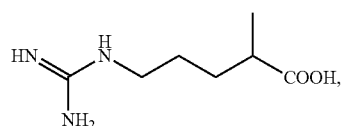 (3a-xvi)
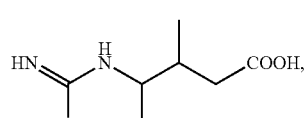 (3a-xvii)
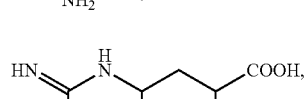 (3a-xviii)
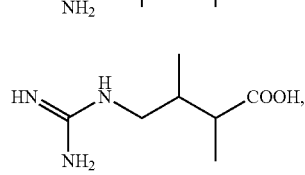 (3a-xix)

(3a-xx)
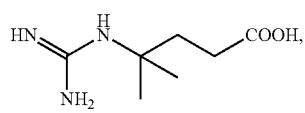
(3a-xxi)
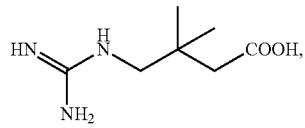
(3a-xxii)
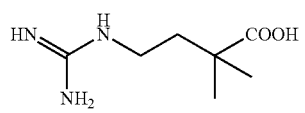
Cases where q represents 1 and Q represents an oxygen atom:
(3b-i)
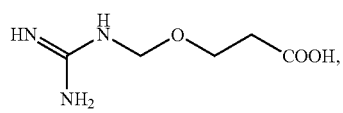
(3b-ii)
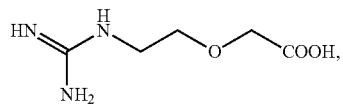
(3b-iii)
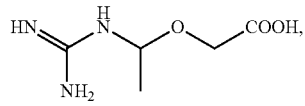
(3b-iv)
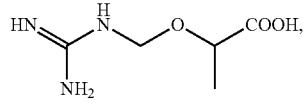
(3b-v)
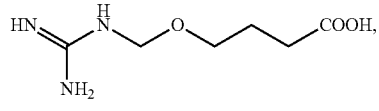
(3b-vi)
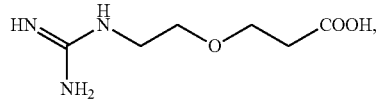
(3b-vii)
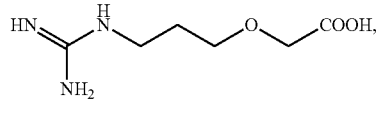
(3b-viii)
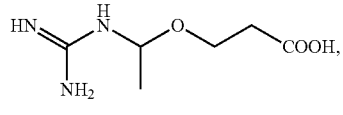
(3b-ix)
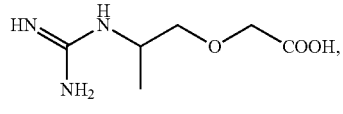
(3b-x)
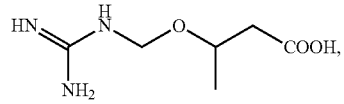
(3b-xi)
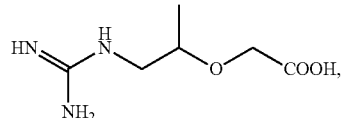
(3b-xii)
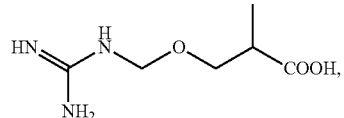
(3b-xiii)
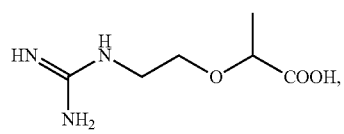
(3b-xiv)
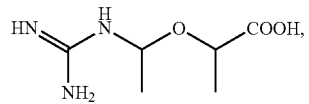
(3b-xv)
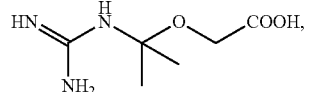
(3b-xvi)
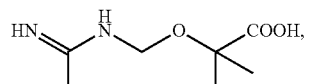
(3b-xvii)
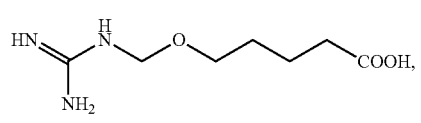
(3b-xviii)
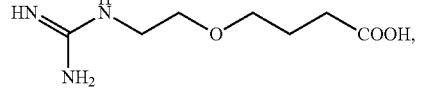
(3b-xix)
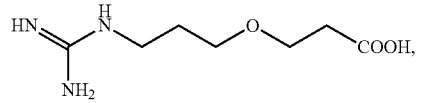
(3b-xx)
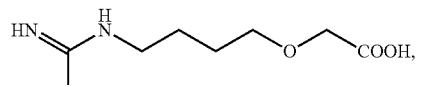
(3b-xxi)
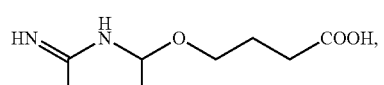
(3b-xxii)
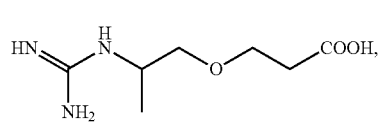

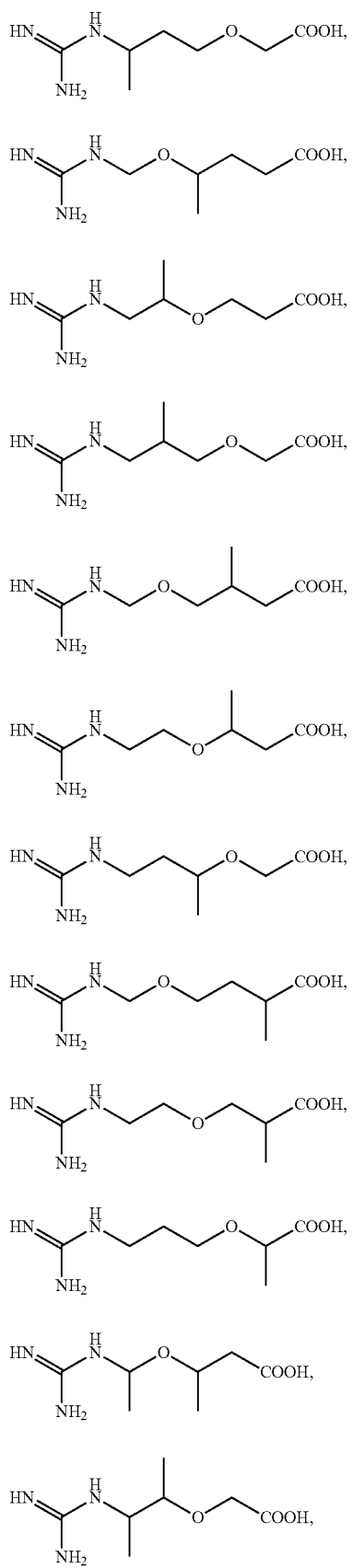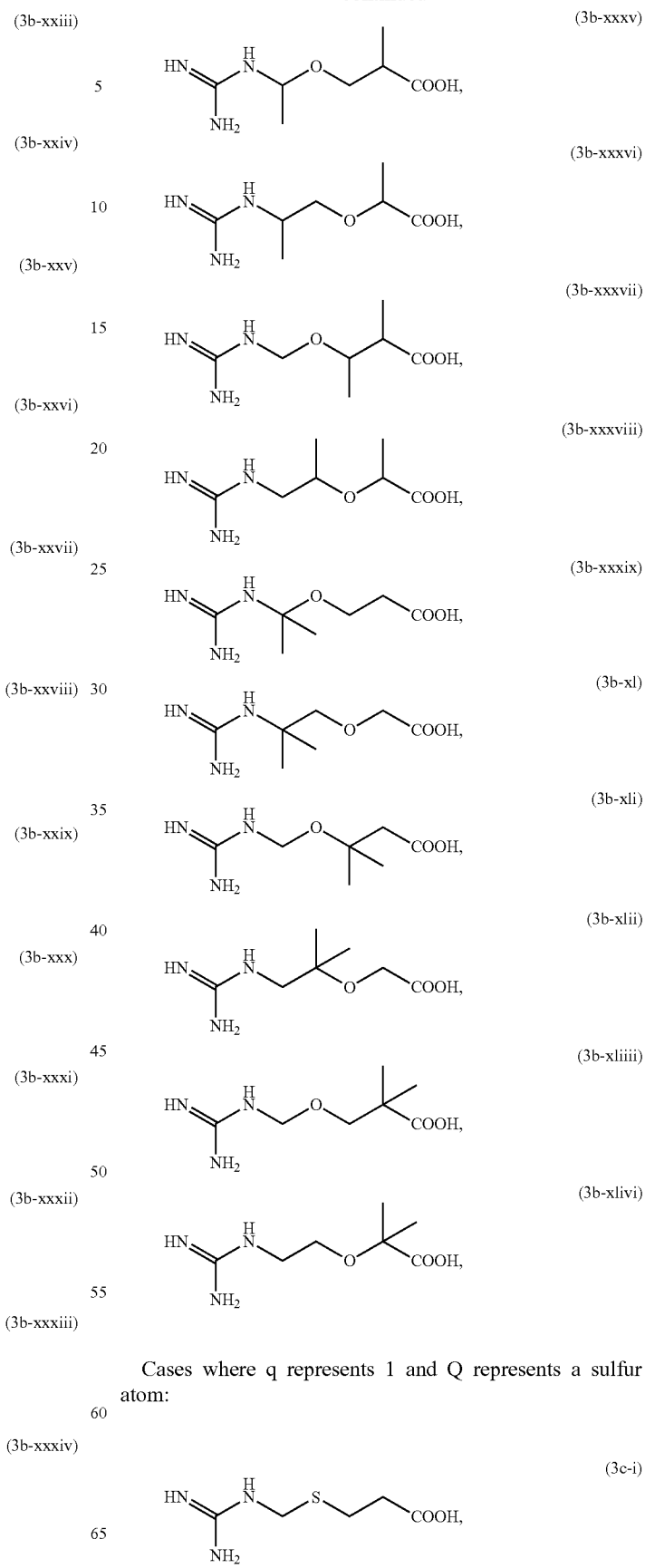
Cases where q represents 1 and Q represents a sulfur atom:

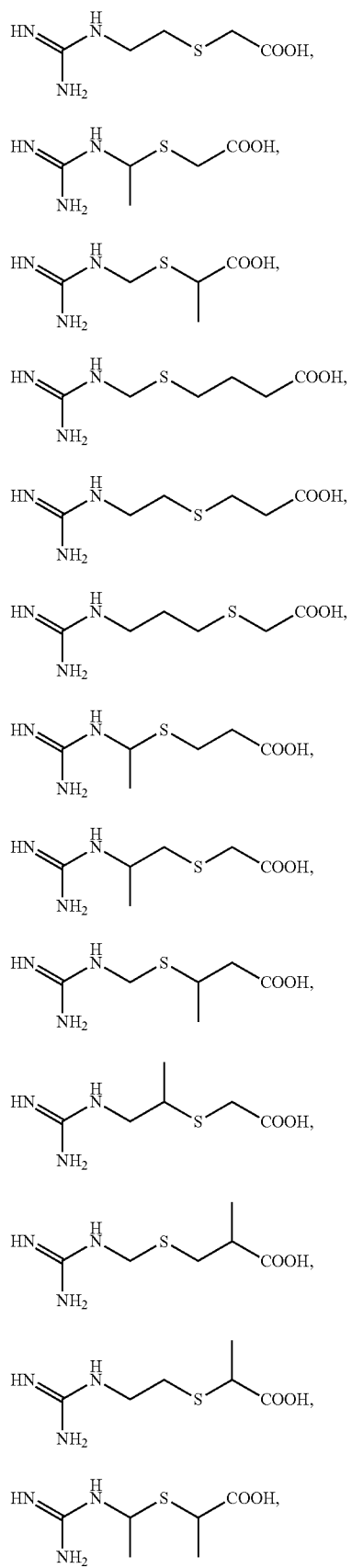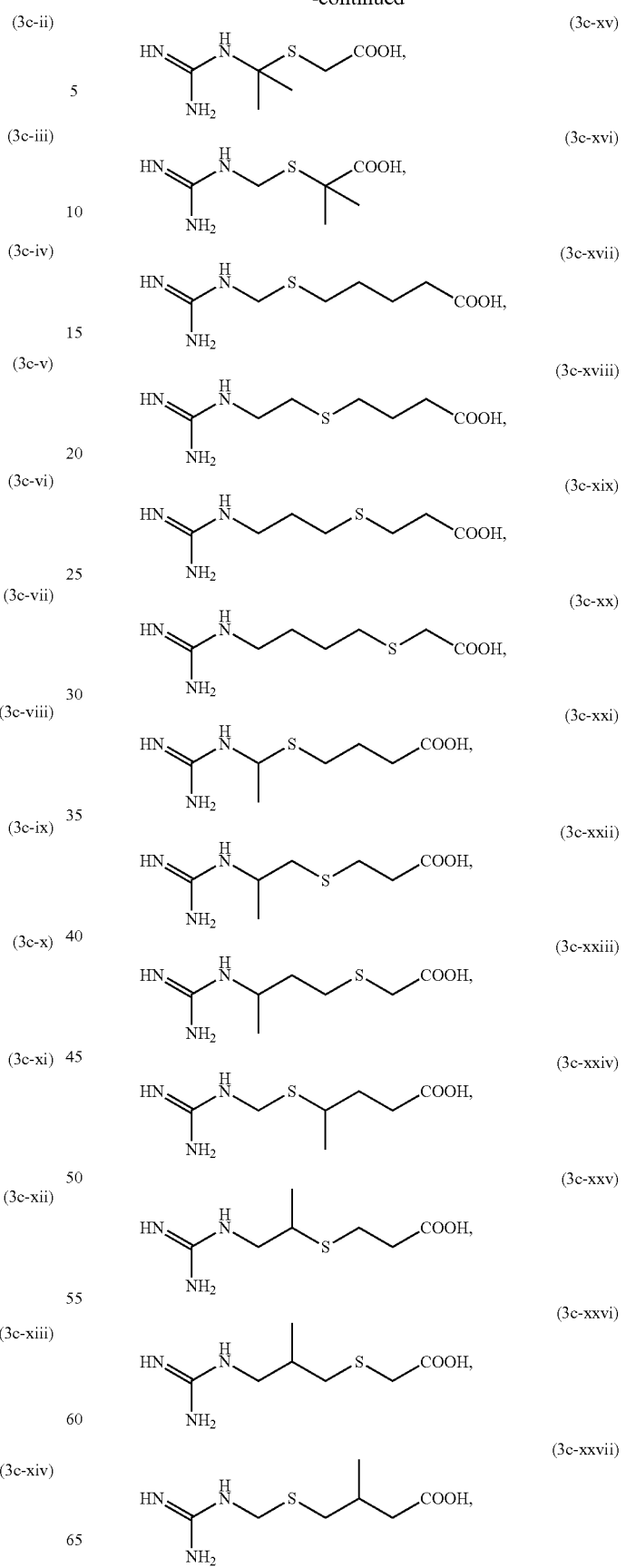

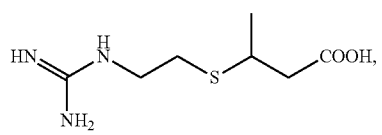
(3c-xxviii)
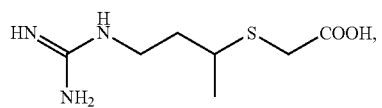
(3c-xxix)
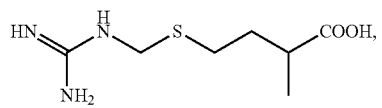
(3c-xxx)
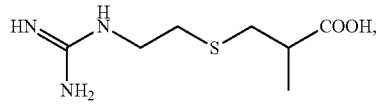
(3c-xxxi)
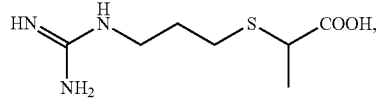
(3c-xxxii)
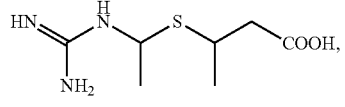
(3c-xxxiii)
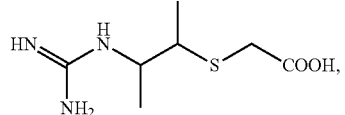
(3c-xxxiv)
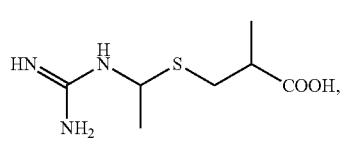
(3c-xxxv)
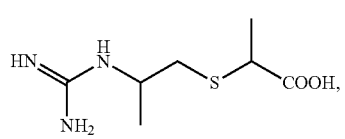
(3c-xxxvi)
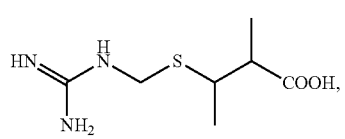
(3c-xxxvii)
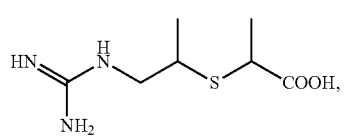
(3c-xxxviii)
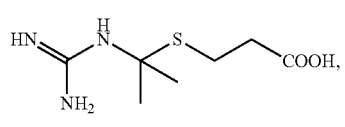
(3c-xxxix)
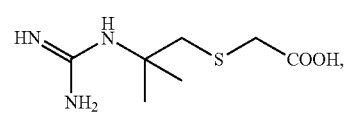
(3c-xl)
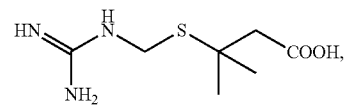
(3c-xli)
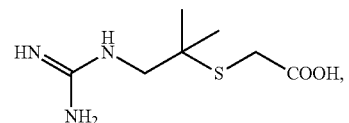
(3c-xlii)
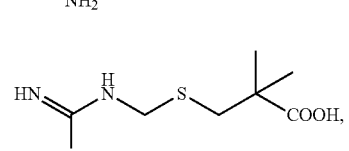
(3c-xliiii)
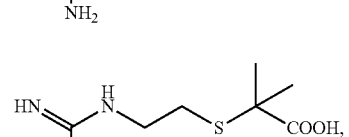
(3c-xlivi)
Specific examples of the compound represented by the general formula (4) are given below.
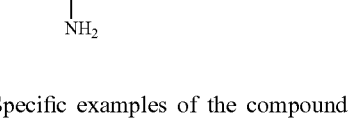
(4-i)
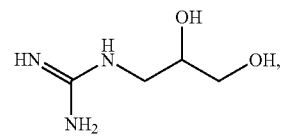
(4-ii)
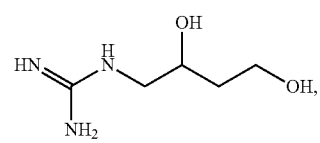
(4-iii)
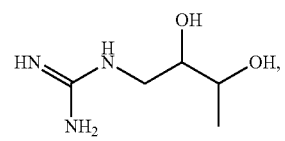
(4-iv)
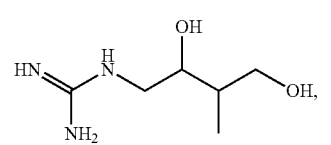
(4-v)

-continued
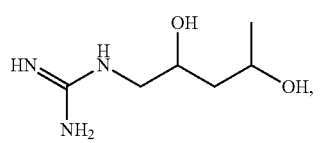
(4-vi)
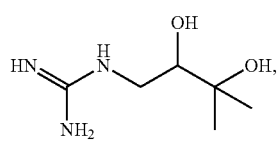
(4-vii)
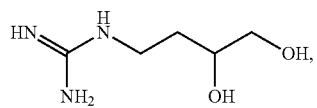
(4-viii)
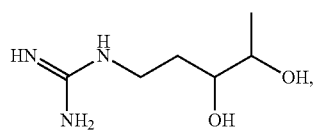
(4-ix)
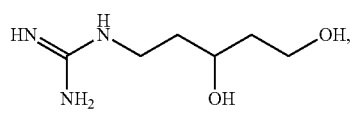
(4-x)
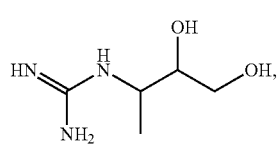
(4-xi)
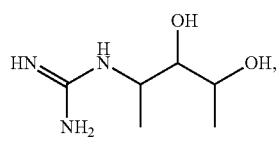
(4-xiii)
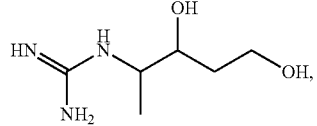
(4-xiii)
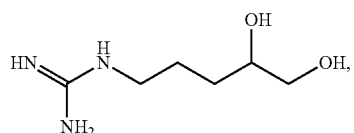
(4-xiv)
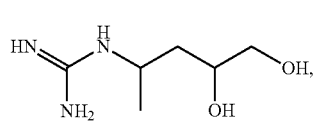
(4-xv)
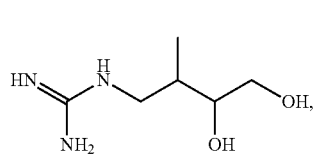
(4-xvi)
-continued
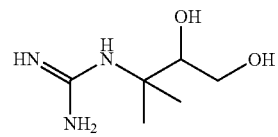
(4-xvii)
Specific examples of the compound represented by the general formula (5) are given below.
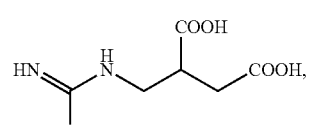
(5-i)
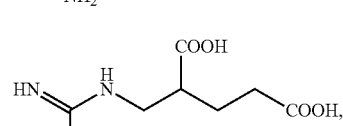
(5-ii)
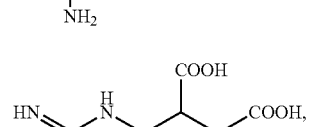
(5-iii)
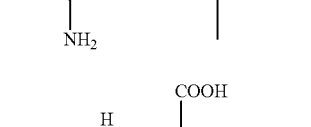
(5-iv)
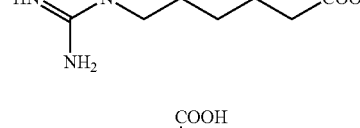
(5-v)
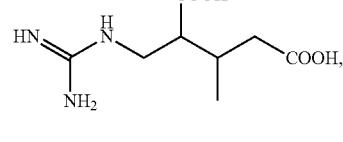
(5-vi)
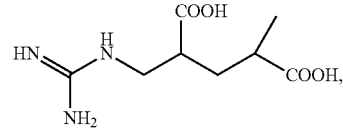
(5-vii)
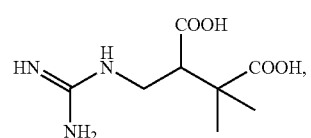
(5-viii)
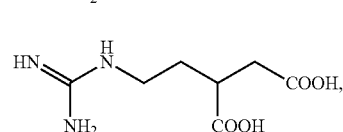
(5-ix)
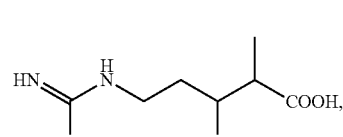

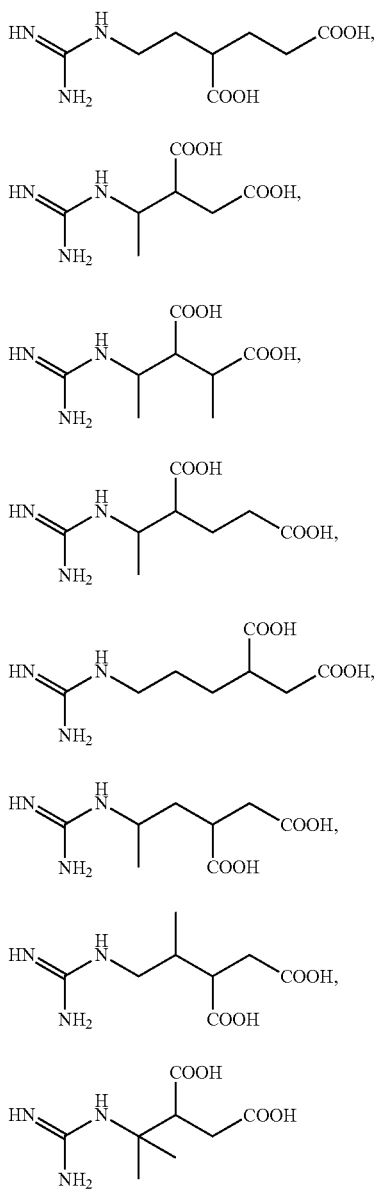

Specific examples of the compound represented by the general formula (6) are given below.

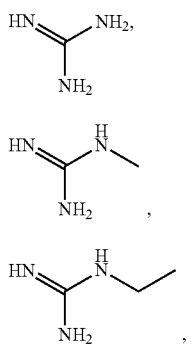

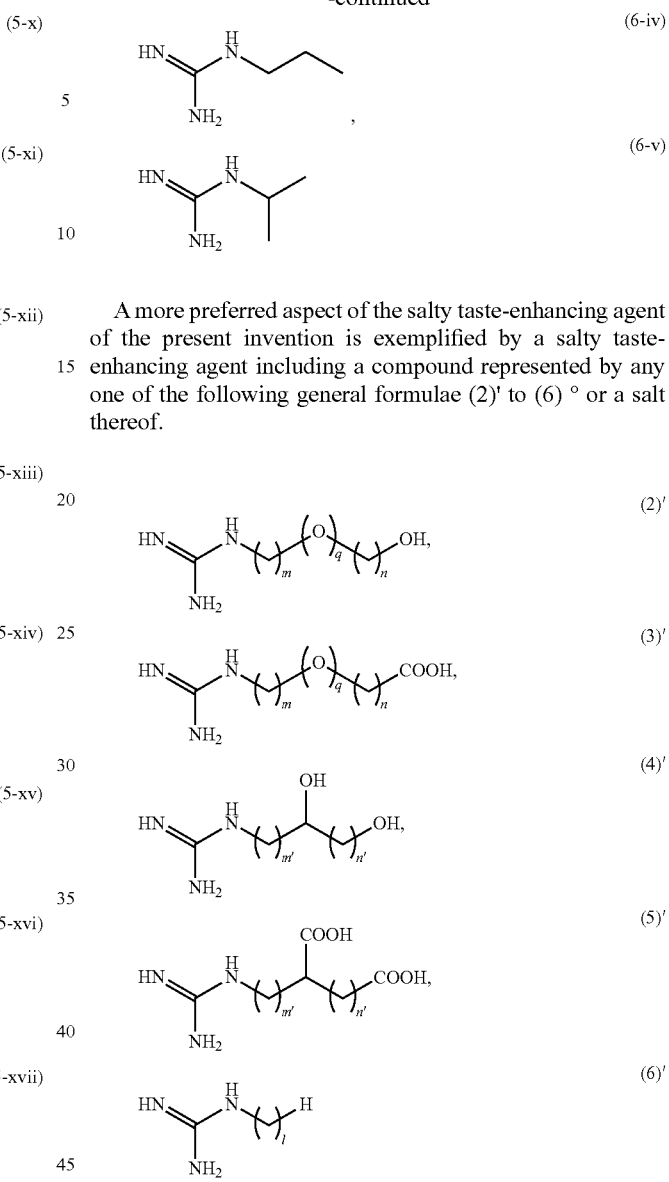

A more preferred aspect of the salty taste-enhancing agent of the present invention is exemplified by a salty taste-enhancing agent including a compound represented by any one of the following general formulae (2)' to (6)° or a salt thereof.

[In the formulae, Q, q, m, n, m',n', and k are the same as those described above.]

A particularly preferred aspect of the salty taste-enhancing agent of the present invention is exemplified by a salty taste-enhancing agent including a compound represented by the following general formula (7) or a salt thereof. The salty taste-enhancing agent including a compound represented by the following general formula (7) or a salt thereof is particularly preferred from the viewpoints that the salty taste-enhancing effect is particularly high and no foreign taste and foreign odor can be sensed.

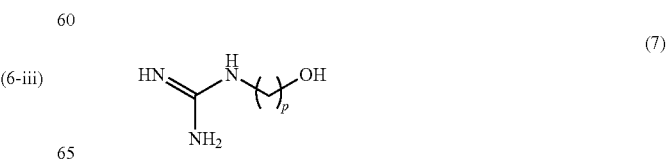

[In the formula, p represents an integer of from 3 to 5.]

Specific examples of the compound represented by the general formula (7) are given below.

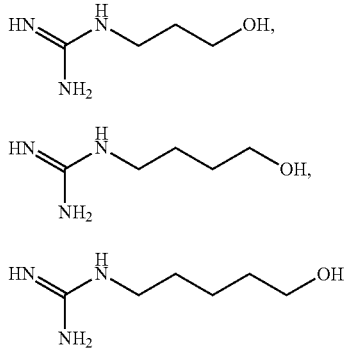

Synthesis Method

The compound represented by the general formula (1) or salt thereof of the present invention may be synthesized, for example, by subjecting a guanidinylation reagent to a reaction with a primary amine compound (X) according to Reaction Scheme-1 (Reaction Formula-1) shown below.

Reaction Scheme-1

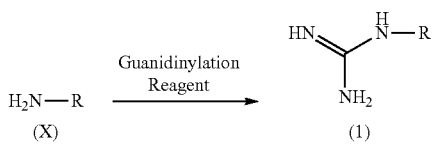

[In the formula, R is as defined above.]

The primary amine compound (X) may be synthesized by a known technique. It should be appreciated that a commercially available product may be used as the compound (X).

A known guanidinylation reagent may be used as the guanidinylation reagent. Suitable examples of the guanidinylation reagent include, but not limited to, 1,3-bis(tert-butoxycarbonyl)-2-(trifluoromethylsulfonyl)guanidine (1,3-bis(tert-butoxycarbonyl)-2-(trifluoromethanesulfonyl) guanidine) (Goodman's reagent), 1-amidinopyrazole hydrochloride, N,N'-bis(tert-butoxycarbonyl)-1H-pyrazole-1-carboxamidine, and N,N'-bis(carbobenzoxy)-1H-pyrazole-1-carboxamidine. The amount of the guanidinylation reagent to be used is generally from about 0.1 mol to an excessive amount, preferably from about 0.8 mol to 2.0 mol, with respect to 1 mol of the compound (X).

It is preferred that the reaction shown in Reaction Scheme-1 be performed in the presence of a base. Examples of the base that may be used include, but not limited to, tertiary amines such as triethylamine, diisopropylethylamine, N,N-dimethylaniline, N,N-dimethylpiperazine, N-methylpiperazine, and pyridine. The amount of the base to be used is generally from 0.8 mol to an excessive amount, preferably from about 1.0 mol to 2.0 mol, with respect to 1 mol of the compound (X).

The reaction shown in Reaction Scheme-1 may be performed in a solvent. The solvent is not particularly limited as long as the progress of the reaction is not inhibited. Specific examples of such solvent include, but not limited to, dichloromethane, chloroform, dimethylformamide, and tetrahydrofuran. One kind of the solvents may be used alone, or two or more kinds thereof may be used as a mixture. Alternatively, when the base is a liquid, the base may be used as the solvent.

The reaction temperature of the reaction shown in Reaction Formula-1 is generally from 0° C. to 150° C., preferably from about 15° C. to 50° C. The reaction time of the reaction shown in Reaction Formula-1 is generally from about 0.1 to 24 hours.

In the case of using a guanidinylation reagent having bonded thereto a protective group, such as 1,3-bis(tert-butoxycarbonyl)-2-(trifluoromethylsulfonyl)guanidine, the removal of the protective group (deprotection reaction) is performed. The deprotection reaction may be performed, for example, under an acidic condition. The "under an acidic condition" is specifically exemplified by, but not limited to, "in the presence of an acid such as hydrochloric acid, sulfuric acid, or trifluoroacetic acid."

The compound represented by the general formula (1) or salt thereof of the present invention may also be synthesized by subjecting S-methylisothiourea or a salt thereof to a reaction with a primary amine compound (X) according to Reaction Scheme-2 (Reaction Formula-2) shown below. The guanidinylation reagent to be used in the synthesis method of Reaction Scheme-1 is expensive, and hence the synthesis method according to Reaction Scheme-2 is more preferred from the viewpoint of cost.

Reaction Scheme-2

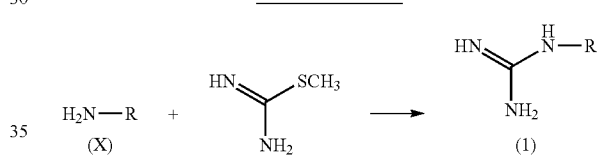

[In the formula, R is as defined above.]

The salt of S-methylisothiourea is not particularly limited as long as the synthesis of the compound represented by the general formula (1) is not inhibited. Examples thereof include salts of organic acids and salts of inorganic acids. Specific examples thereof include a hydrochloride, a sulfate, a nitrate, an acetate, a trichloroacetate, and a formate. Of those, a sulfate is preferred from the viewpoint of easy availability.

The amount of S-methylisothiourea or the salt thereof to be used is generally from about 0.1 to 10 mol, preferably from about 0.5 to 3.0 mol, with respect to 1 mol of the compound (X).

The reaction shown in Reaction Scheme-2 may be performed in the absence of a solvent or in a solvent. The solvent is not particularly limited as long as the progress of the reaction is not inhibited. The solvent is specifically exemplified by, but not limited to, water.

The reaction temperature of the reaction shown in Reaction Scheme-2 is generally from 0 to 200° C., preferably from about 50 to 150° C. The reaction time of the reaction shown in Reaction Scheme-2 is generally from about 10 minutes to 24 hours.

When the salt of S-methylisothiourea is used in the reaction shown in Reaction Scheme-2, a corresponding salt of the compound represented by the general formula (1) is generally obtained as a product. For example, when S-methylisothiourea sulfate is used, a sulfate of the compound represented by the general formula (1) is obtained as a product. In this case, the salt of the compound represented by the general formula (1) to be obtained may be used as it is, or may be converted to another acid salt, as necessary.

A technique for the conversion is not particularly limited. For example, in the case of converting a sulfate to a hydrochloride, there may be employed a technique involving:

converting a sulfate to a mixture of a hydrochloride and the sulfate by adding about 0.1 to 100 mol, preferably about 1 to 10 mol of sodium chloride (NaCl) or calcium chloride (CaCl$_2$) with respect to 1 mol of the sulfate in the presence of silica gel; and isolating and purifying only the hydrochloride from the resultant mixture by means of differences in physical properties (e.g., solubility in a solvent) between the sulfate and the hydrochloride. In an alternative aspect, there may be employed a technique involving: converting a sulfate to a corresponding organic acid salt by performing elution using a solution containing an organic acid (e.g., acetic acid or formic acid) as a mobile phase in a chromatography method (e.g., silica gel is used as a carrier); and converting the resultant organic acid salt to a hydrochloride by azeotropy with an excessive amount of hydrochloric acid.

A product to be obtained through the reaction shown in Reaction Formula-1 or the reaction shown in Reaction Formula-2 may be isolated and purified by means to be generally performed. Examples of such means include, but not limited to, a recrystallization method, a distillation method, and a chromatography method.

Thus, the compound represented by the general formula (1) or the salt thereof is produced. The synthesis of the compound may be confirmed, for example, by known means such as $^1$H-NMR measurement, $^{13}$C-NMR measurement, or mass spectrometry (e.g., electrospray ionization mass spectrometry (MS-ESI)).

When the compound represented by the general formula (1) or the salt thereof is available as a commercially available product, the commercially available product may also be used.

The salty taste-enhancing agent of the present invention exhibits a salty taste-enhancing action of allowing a salty taste of salt to be strongly sensed. The salty taste-enhancing action may be evaluated by a sensory test. An example of the sensory test is a method involving comparing salty taste intensities of a salt aqueous solution at a predetermined concentration (e.g., 0.7 wt %) (control) and a salt aqueous solution at the same concentration containing an ingredient to be tested (Sample A) When the ingredient to be tested has a salty taste-enhancing action, a stronger salty taste is sensed in Sample A as compared to the control.

In addition, in evaluating the salty taste-enhancing action, the salty taste-enhancing action may be quantified by: comparing salty taste intensities of a salt aqueous solution containing an ingredient to be tested (Sample B) and a salt aqueous solution group (control group) at a higher concentration than that of Sample B; and searching a salt concentration at which a salty taste equal to that of Sample B is sensed.

In order that the salty taste-enhancing agent of the present invention may exhibit an effect, it is necessary to use the salty taste-enhancing agent in combination with salt. However, most of foods and beverages required to have a reduced salt content, such as a seasoning or soup, originally contain salt. Thus, the salty taste-enhancing agent can exhibit a salty taste-enhancing effect by coexisting with salt contained in the foods and beverages. Besides, the salty taste-enhancing agent of the present invention is hardly accompanied by foreign taste and foreign odor, which have been considered as problems in the related art. That is, the coexistence of the salty taste-enhancing agent of the present invention with salt in a food and beverage can achieve both of a reduced salt content and high food palatability.

The food and beverage is not particularly limited, and examples thereof include: seasonings such as soy sauce, miso sauce, and ketchup; seasonings containing hydrolyzed animal and vegetable proteins (HAP and HVP), yeast extract, amino acids, peptides, and the like as main ingredients; seasoning foods to be used for seasoning of foods, such as soup powder, seasoning soy sauce, tare sauce, roux, and dressing; processed cereals such as noodles, bread, and snacks; processed meat and fish such as ham and sausages and surimi; soup; pickles; and daily dishes. In addition, the food and beverage includes instant foods that may be cooked by addition of hot water or water (e.g., powder and liquid soup for instant noodles, instant consommé soup, potage soup, Chinese soup, miso soup, suimono, and soup-type instant noodles).

The amount of the salty taste-enhancing agent of the present invention to be added to the food and beverage is not particularly limited. The food and beverage required to have a reduced salt content generally has added thereto about 0.2 to 2.0 wt %, particularly about 0.5 to 1.5 wt % of salt in terms of a concentration at the time of food and beverage intake. The salty taste-enhancing agent of the present invention can exhibit a salty taste-enhancing action when added at, for example, 1 ppm or more, preferably 10 ppm or more, particularly preferably 15 ppm or more at the time of food and beverage intake, with respect to the salt contained in the food and beverage in such amount as described above. The upper limit is not particularly limited, but may be set to 20% or less, preferably 5% or less from the viewpoints of solubility and taste property.

The salty taste-enhancing agent of the present invention may be provided in the form of only the above-mentioned compound, or may be provided in the form of a solid composition or a liquid composition. The salty taste-enhancing agent, when provided as the composition, may contain an additive that may be used for production of foods and beverages, such as an excipient, a dye, or a flavor, as necessary, as long as the salty taste-enhancing action is not inhibited.

The salty taste-enhancing agent of the present invention may be provided as a food additive including the above-mentioned compound or salt thereof, for example.

2. Seasoning, and Food and Beverage

The present invention also provides a seasoning including the above-mentioned compound or salt thereof (salty taste-enhancing agent of the present invention).

The above-mentioned compound or salt thereof refers to the salty taste-enhancing agent of the present invention described in the above-mentioned Section "1."

The seasoning of the present invention is not particularly limited as long as the seasoning includes the above-mentioned compound or salt thereof and may be used for seasoning of foods. Specific aspects thereof are exemplified by, but not limited to: soy sauce, miso sauce, and ketchup; seasonings containing hydrolyzed animal and vegetable proteins (HAP and HVP), yeast extract, amino acids, peptides, and the like as main ingredients; and soup powder, seasoning soy sauce, tare sauce, roux, and dressing.

From the viewpoint that the above-mentioned compound or salt thereof exhibits a salty taste-enhancing effect by coexisting with sodium chloride (salt), as a preferred aspect of the seasoning of the present invention, there is given an aspect including sodium chloride. Such aspect also encompasses: a seasoning including the above-mentioned compound or salt thereof (salty taste-enhancing agent of the present invention) and sodium chloride; and a seasoning obtained by blending such seasoning with an additive that may be used for production of foods and beverages, such as an excipient, a dye, or a flavor, as necessary.

In the seasoning of the present invention, the content of the above-mentioned compound or salt thereof only needs to be 1 ppm or more, preferably 10 ppm or more, particularly preferably 15 ppm or more at the time of food and beverage intake. When the seasoning of the present invention contains sodium chloride, the content of sodium chloride only needs to be from about 0.1 to 2.0 wt %, particularly from about 0.3 to 1.5 wt % at the time of food and beverage intake.

The present invention also provides a food and beverage including the above-mentioned compound or salt thereof (salty taste-enhancing agent of the present invention). As a preferred aspect thereof, there is given a food and beverage having added thereto the above-mentioned compound or salt thereof. Herein, the term "added" refers to that the above-mentioned compound or salt thereof is not derived from a raw material for a food and beverage, but is separately added.

A specific aspect of the food and beverage is not particularly limited. Specific examples of the food and beverage include: processed cereals such as noodles, bread, and snacks; processed meat and fish such as ham and sausages and surimi; soup; pickles; and daily dishes. In addition, the food and beverage includes instant foods that may be cooked by addition of hot water or water (e.g., powder and liquid soup for instant noodles, instant consommé soup, potage soup, Chinese soup, miso soup, suimono, and soup-type instant noodles).

As a preferred aspect of the food and beverage of the present invention, there is given an aspect including sodium chloride.

In the food and beverage of the present invention, the content of the above-mentioned compound or salt thereof only needs to be 1.0 ppm or more, preferably 10.0 ppm or more, particularly preferably 15 ppm or more at the time of food and beverage intake. When the food and beverage of the present invention contains sodium chloride, the content of sodium chloride only needs to be from about 0.1 to 2.0 wt %, particularly from about 0.3 to 1.5 wt % at the time of food and beverage intake.

3. Salty Taste-Enhancing Method for Food and Beverage

The present invention also provides a salty taste-enhancing method for a food and beverage. The method of the present invention includes a step of adding the above-mentioned compound or salt thereof to a food and beverage.

The food and beverage is not particularly limited. Specifically, as the food and beverage, the ones described in the above-mentioned Section "2." It is preferred that the food and beverage contain sodium chloride (salt).

The above-mentioned compound or salt thereof refers to the salty taste-enhancing agent of the present invention described in the above-mentioned Section "1."

A specific technique for adding the compound or the salt thereof to the food and beverage is not particularly limited. The compound or the salt thereof may be blended as one of the raw materials during the preparation of the food and beverage, or may be added to the food and beverage immediately before food and beverage intake. The amount of the compound or the salt thereof to be added is not particularly limited. However, the compound or the salt thereof is added so that its content in the food and beverage is 1 ppm or more, preferably 10 ppm or more, particularly preferably 15 ppm or more at the time of food and beverage intake.

Thus, the salty taste of the food and beverage is enhanced.

EXAMPLES

The present invention is hereinafter described in more detail by way of Examples. The present invention is by no means limited thereto.

It should be noted that each measurement was performed using an apparatus shown below.

$^1$H-NMR and $^{13}$C-NMR measurements: Inova 500 manufactured by Varian, Inc.

MS-ESI measurement: JMS-T100LC AccuTOF manufactured by JEOL Ltd.

Synthesis Example 1

4-Guanidino-1-butanol hydrochloride (a)

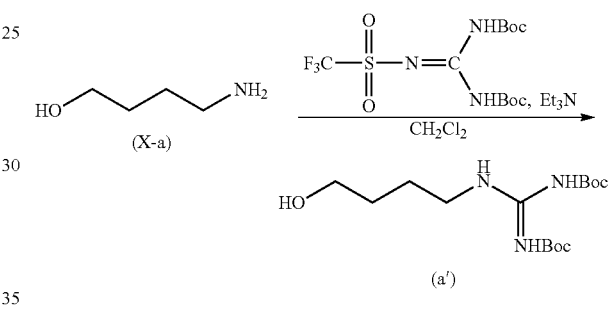

4-Amino-1-butanol (X-a) (1 g, 11.2 mmol) was dissolved in dichloromethane (25 ml). Triethylamine (1.14 g, 11.2 mmol, 1.0 equivalent) was added thereto, and the mixture was stirred at room temperature.

1,3-Bis(tert-butoxycarbonyl)-2-(trifluoromethanesulfonyl) guanidine (3.95 g, 10.1 mmol, 0.9 equivalent) dissolved in dichloromethane (25 ml) was added dropwise thereto, and the mixture was further stirred at room temperature for 1 hour. The reaction was quenched by adding water. After that, the aqueous layer was extracted with ethyl acetate, and the organic layer was washed with a saturated sodium bicarbonate aqueous solution and saturated saline, and then dried over anhydrous sodium sulfate. The solvent was removed with an evaporator, and then the residue was purified by silica gel chromatography (n-hexane:ethyl acetate=10:1→2:1) to afford 3.32 g (10.0 mmol, 89.3%) of (a') as white powder.

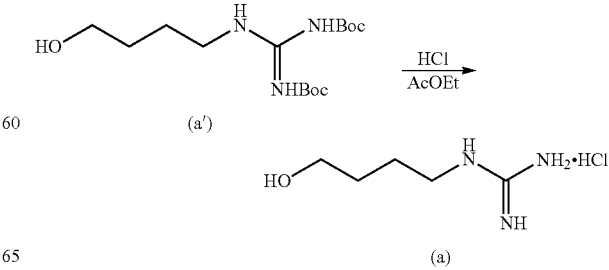

(a') (2.85 g, 8.60 mmol) was dissolved in 10 ml of ethyl acetate. Concentrated hydrochloric acid (10 ml) was added dropwise thereto, and the mixture was stirred at room temperature for 2 hours, and azeotroped with methanol. After that, the residue was extracted with dilute hydrochloric acid and washed with dichloromethane, and then the aqueous layer was azeotroped with methanol to afford white powder. The white powder was washed with ethyl acetate to afford 817 mg (4.87 mmol, 56.7%) of 4-guanidino-1-butanol hydrochloride (a) as white powder.

$^1$H-NMR (CD$_3$OD, 500 MHz): δ=1.55-1.70 (m, 4H), 3.21 (t, 2H, J=7.0 Hz), 3.58 (t, 2H, J=7.0 Hz)

$^{13}$C-NMR (CD$_3$OD, 125 MHz): δ=26.5, 30.4, 42.3, 62.3, 158.5

MS-ESI (C$_5$H$_{14}$ON$_3$Cl) 2M+HCl+H: 299.21 (calculated value: 299.20).

Synthesis Example 2

3-Guanidino-1-propanol hydrochloride (b)

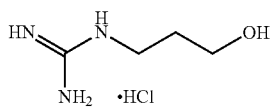

282.4 mg (1.84 mmol, 92.1%) of 3-guanidino-1-propanol hydrochloride (b) were obtained as a colorless oily substance in the same manner as in Synthesis Example 1 except that 3-amino-1-propanol (x-b) (150 mg, 2.00 mmol) was used and the washing with ethyl acetate was not performed.

$^1$H-NMR (CD$_3$OD, 500 MHz): δ=1.75 (tt, 2H, J=6.0, 6.0 Hz), 3.25 (t, 2H, J=6.0 Hz), 3.60 (t, 2H, J=6.0 Hz)

$^{13}$C-NMR (CD$_3$OD, 125 MHz): δ=32.4, 39.5, 59.7, 158.8

MS-ESI (C$_4$H$_{12}$ON$_3$Cl): 2M+HCl+H: 271.17 (calculated value: 271.17).

Synthesis Example 3

5-Guanidino-1-pentanol hydrochloride (c)

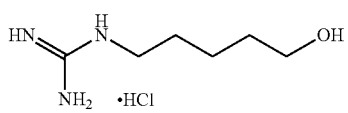

250.0 mg (1.38 mmol, 68.9%) of 5-guanidino-1-pentanol hydrochloride (c) were obtained as a colorless oily substance in the same manner as in Synthesis Example 1 except that 5-amino-1-pentanol (x-c) (206 mg, 2.00 mmol) was used and the washing with ethyl acetate was not performed.

$^1$H-NMR (CD$_3$OD, 500 MHz): δ=1.40-1.48 (m, 2H), 1.57 (tt, 2H, J=6.8, 6.8 Hz), 1.62 (tt, 2H, J=6.8, 6.8 Hz), 3.18 (t, 2H, J=6.8 Hz), 3.57 (t, 2H, J=6.8 Hz)

$^{13}$C-NMR (CD$_3$OD, 125 MHz): δ=24.0, 29.6, 33.0, 42.4, 62.6, 158.6

MS-ESI (C$_6$H$_{16}$ON$_3$Cl): 2M+HCl+H: 327.24 (calculated value: 327.23).

Synthesis Example 4

2-Guanidinoethanol Hydrochloride (d)

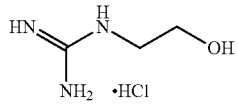

247.5 mg (1.77 mmol, 88.8%) of 2-guanidinoethanol hydrochloride (d) were obtained as a colorless oily substance in the same manner as in Synthesis Example 1 except that 2-aminoethanol (x-d) (122 mg, 2.00 mmol) was used and the washing with ethyl acetate was not performed.

$^1$H-NMR (CD$_3$OD, 500 MHz): δ=3.33 (t, 2H, J=5.1 Hz), 3.69 (t, 2H, J=5.1 Hz)

$^{13}$C-NMR (CD$_3$OD, 125 MHz): δ=45.1, 61.4, 159.3

MS-ESI (C$_3$H$_{10}$ON$_3$Cl): 2M+HCl+H: 243.13 (calculated value: 243.13).

Synthesis Example 5

6-Guanidino-1-hexanol hydrochloride (e)

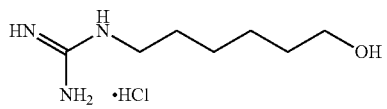

368.7 mg (1.88 mmol, 94.4%) of 6-guanidino-1-hexanol hydrochloride (e) were obtained as a colorless oily substance in the same manner as in Synthesis Example 1 except that 6-amino-1-hexanol (x-e) (234 mg, 2.00 mmol) was used and the washing with ethyl acetate was not performed.

$^1$H-NMR (CD$_3$OD, 500 MHz): δ=1.37-1.46 (m, 4H), 1.52-1.58 (m, 2H), 1.58-1.64 (m, 2H), 3.19 (t, 2H, J=6.6 Hz), 3.55 (t, 2H, J=6.6 Hz)

$^{13}$C-NMR (CD$_3$OD, 125 MHz): δ=26.5, 27.5, 29.8, 33.4, 42.4, 62.8, 158.6

MS-ESI (C$_7$H$_{18}$ON$_3$Cl): 2M+HCl+H: 355.26 (calculated value: 355.26).

Synthesis Example 6

(±)-1-Guanidino-2-Propanol hydrochloride (f)

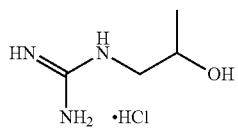

435.2 mg (2.83 mmol, 53.2%) of (±)-1-guanidino-2-propanol hydrochloride (f) were obtained as a colorless oily substance in the same manner as in Synthesis Example 1 except that (±)-1-amino-2-propanol (x-f) (400 mg, 5.33 mmol) was used and the washing with ethyl acetate was not performed.

¹H-NMR (CD₃OD, 500 MHz): δ=1.19 (d, 3H, J=6.9 Hz), 3.09 (dd, 1H, J=8.6, 12.8 Hz), 3.23-3.32 (m, 1H), 3.88-3.93 (m, 1H) ¹³C-NMR (CD₃OD, 125 MHz): δ=20.7, 49.7, 67.1, 159.3.

Synthesis Example 7

(S)-2-Guanidino-1-Propanol Hydrochloride (g)

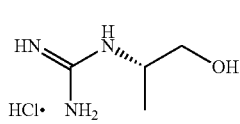

432.9 mg (2.82 mmol, 52.9%) of (S)-2-guanidino-1-propanol hydrochloride (g) were obtained as a colorless oily substance in the same manner as in Synthesis Example 1 except that (S)-(+)-2-amino-1-propanol (x-g) (400 mg, 5.33 mmol) was used and the washing with ethyl acetate was not performed.

¹H-NMR (CD₃OD, 500 MHz): δ=1.20 (d, 3H, J=8.1 Hz), 3.47 (dd, 1H, J=8.1, 12.1 Hz), 3.59-3.63 (m, 1H), 3.64-3.70 (m, 1H) ¹³C-NMR (CD₃OD, 125 MHz): δ=17.1, 51.3, 66.3, 158.6.

Synthesis Example 8

3-Guanidino-2,2-dimethyl-1-propanol hydrochloride (h)

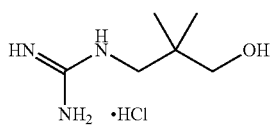

120.1 mg (0.66 mmol, 68.2%) of 3-guanidino-2,2-dimethyl-1-propanol hydrochloride (h) were obtained as a colorless oily substance in the same manner as in Synthesis Example 1 except that 3-amino-2,2-dimethyl-1-propanol (x-h) (100 mg, 0.97 mmol) was used and the washing with ethyl acetate was not performed.

¹H-NMR (CD₃OD, 500 MHz): δ=0.93 (s, 6H), 3.08 (s, 2H), 3.32 (s, 2H)
¹³C-NMR (CD₃OD, 125 MHz): δ=22.6 (×2), 37.4, 49.7, 68.8, 159.4
MS-ESI (C₆H₁₆ON₃Cl) 2M+HCl+H: 327.20 (calculated value: 327.23).

Synthesis Example 9

2-(2-Guanidinoethoxy)ethanol hydrochloride (i)

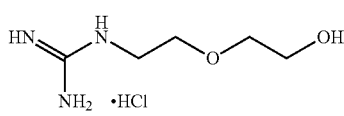

577.8 mg (3.15 mmol, 82.7%) of 2-(2-guanidinoethoxy) ethanol hydrochloride (i) were obtained as a colorless oily substance in the same manner as in Synthesis Example 1 except that 2-(2-aminoethoxy)ethanol (x-i) (400 mg, 3.80 mmol) was used and the washing with ethyl acetate was not performed.

¹H-NMR (CD₃OD, 500 MHz): δ=3.39 (t, 2H, J=5.0 Hz), 3.59 (t, 2H, J=5.0 Hz), 3.63 (t, 2H, J=5.0 Hz), 3.69 (t, 2H, J=5.0 Hz) ¹³C-NMR (CD₃OD, 125 MHz): δ=43.0, 62.1, 70.5, 73.6, 159.2.

Synthesis Example 10

2-(2-Guanidinoethylthio)ethanol hydrochloride (j)

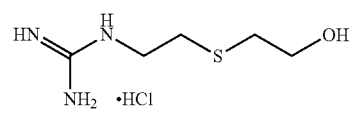

541.6 mg (2.71 mmol, 82.2%) of 2-(2-guanidinoethylthio)ethanol hydrochloride (j) were obtained as a colorless oily substance in the same manner as in Synthesis Example 1 except that 2-(2-aminoethylthio)ethanol (x-j) (400 mg, 3.30 mmol) was used and the washing with ethyl acetate was not performed.

¹H-NMR (CD₃OD, 500 MHz): δ=2.72 (t, 2H, J=6.1 Hz), 2.78 (t, 2H, J=6.8 Hz), 3.42 (t, 2H, J=6.8 Hz), 3.72 (t, 2H, J=6.1 Hz) ¹³C-NMR (CD₃OD, 125 MHz): δ=32.2, 35.3, 42.3, 62.7, 158.7.

Synthesis Example 11

(R)-3-Guanidino-1,2-propanediol hydrochloride (k)

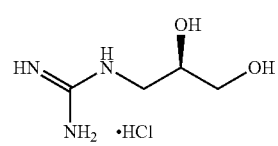

628.5 mg (3.71 mmol, 84.4%) of (R)-3-guanidino-1,2-propanediol hydrochloride (k) were obtained as white powder in the same manner as in Synthesis Example 1 except that (R)-3-amino-1,2-propanediol (x-k) (400 mg, 4.39 mmol) was used.

¹H-NMR (CD₃OD, 500 MHz): δ=3.24 (dd, 1H, J=6.7, 14.1 Hz), 3.37 (dd, 1H, J=4.0, 14.1 Hz), 3.51 (dd, 1H, J=6.0, 12.1 Hz), 3.56 (dd, 1H, J=6.0, 12.1 Hz), 3.74-3.80 (m, 1H) ¹³C-NMR (CD₃OD, 125 MHz): δ=45.5, 64.4, 71.6, 159.5.

Synthesis Example 12

1-Guanidinopropane Hydrochloride (l)

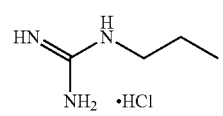

597.2 mg (4.34 mmol, 85.5%) of 1-guanidinopropane hydrochloride (1) were obtained as a colorless oily substance in the same manner as in Synthesis Example 1 except that propylamine (x-1) (300 mg, 5.08 mmol) was used and the washing with ethyl acetate was not performed.

$^1$H-NMR (CD$_3$OD, 500 MHz): δ=0.98 (t, 3H, J=7.7 Hz), 1.61 (tq, 2H, J=7.7, 7.7 Hz), 3.15 (t, 2H, J=7.7 Hz)

$^{13}$C-NMR (CD$_3$OD, 125 MHz): δ=11.5, 23.2, 44.0, 158.6

MS-ESI (C$_4$H$_{12}$N$_3$Cl): 2M+HCl+H: 239.14 (calculated value: 239.18).

Synthesis Example 13

Synthesis of 3-Guanidino-1-Propanol Hydrochloride (b) Using S-Methylisothiourea Sulfate

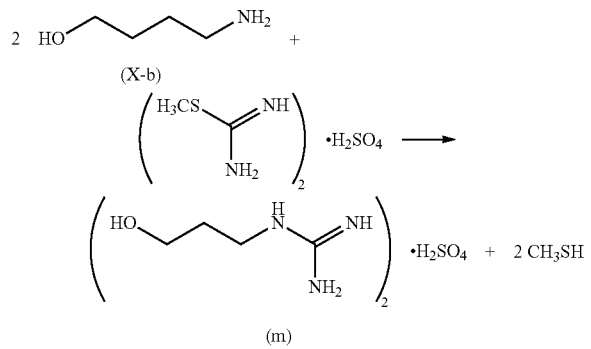

3-Amino-1-propanol (X-b) (150 mg, 2.0 mmol) was dissolved in water (0.4 ml)). S-Methylisothiourea sulfate (278 mg, 1.0 mmol) was added thereto to be suspended, and then the mixture was heated to reflux for 6 hours. Water and the remaining 3-amino-1-propanol were removed with an evaporator to afford 344 mg of 3-guanidino-1-propanol sulfate (m) as an oily crude product.

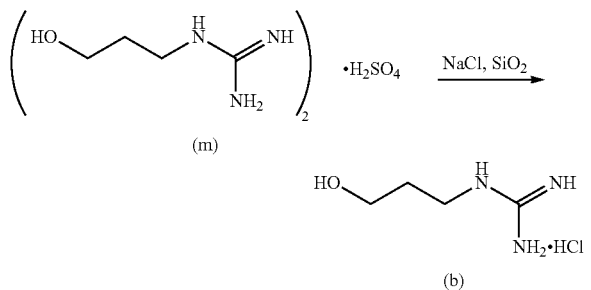

To 344 mg of 3-guanidino-1-propanol sulfate (m) as the crude product, 1.04 ml of a 3 M NaCl aqueous solution were added to be suspended. To the resultant suspension were added 10 ml of methanol and further added 2.0 g of silica gel (Wakogel C-200). After that, the solvent was removed with an evaporator to adsorb the sample onto silica gel. Thus, a sample gel was prepared. 14.1 g of a separation gel (Wakogel C-200) were suspended in acetone and filled into a glass column. The sample gel was mounted onto the column, 50 ml of acetone were passed through the column, and then 200 ml of ethanol were passed through the column. The eluted ethanol layer was evaporated to dryness with an evaporator to afford 241 mg (1.57 mmol, 78.5%) of 3-guanidino-1-propanol hydrochloride (b) as a colorless oily substance.

$^1$H-NMR and $^{13}$C-NMR data on the resultant colorless oily substance were both consistent with those on 3-guanidino-1-propanol hydrochloride (b) obtained in Synthesis Example 2.

Synthesis Example 14

3-Guanidino-1-Propanol Sulfate (m)

To 344 mg of crude 3-guanidino-1-propanol sulfate (m) were added 10 ml of methanol and further added 2.0 g of silica gel (Wakogel C-200), and then the solvent was removed with an evaporator to adsorb the sample onto silica gel. Thus, a sample gel was prepared. 14.1 g of a separation gel (Wakogel C-200) were suspended in acetone and filled into a glass column. The sample gel was mounted onto the column, 50 ml of acetone and 50 ml of ethanol were passed through the column, and then 200 ml of methanol were passed through the column. The eluted methanol layer was evaporated to dryness with an evaporator to afford 235 mg (1.41 mmol, 70.5%) of 3-guanidino-1-propanol sulfate (m) as a colorless oily substance.

$^1$H-NMR (CD$_3$OD, 500 MHz): δ=1.79 (tt, 2H, J=6.0, 6.0 Hz), 3.27 (t, 2H, J=6.0 Hz), 3.63 (t, 2H, J=6.0 Hz)

$^{13}$C-NMR (CD$_3$OD, 125 MHz): δ=32.5, 39.2, 59.6, 158.9

Example 1

Sensory Evaluation

The compounds synthesized in Synthesis Examples 1 to 11 and Synthesis Example 14, and commercially available products of guanidine hydrochloride, β-guanidinopropanoic acid, γ-guanidinobutyric acid, and 6-guanidinocaproic acid were used as evaluation samples and evaluated for their salty taste-enhancing actions.

Each evaluation sample and sodium chloride (salt) were dissolved in distilled water to prepare an aqueous solution containing 0.150 wt % of the evaluation sample and 0.700 wt % of sodium chloride, which was used as an evaluation solution. In addition, solutions containing 0.700 wt %, 0.735 wt %, 0.770 wt %, 0.805 wt %, and 0.840% of sodium chloride were used as comparative objects.

Each evaluation sample was subjected to sensory evaluation based on the following criteria.

++++: exhibiting a salty taste equal to or stronger than that of 0.840 wt % saline (exhibiting a salty taste-enhancing effect of 20% or more);

+++: exhibiting a salty taste equal to or stronger than that of 0.805 wt % saline (exhibiting a salty taste-enhancing effect of 15% or more);

++: exhibiting a salty taste equal to or stronger than that of 0.770 wt % saline (exhibiting a salty taste-enhancing effect of 10% or more);

+: exhibiting a salty taste equal to or stronger than that of 0.735 wt % saline (exhibiting a salty taste-enhancing effect of 5% or more); and ±: exhibiting a salty taste weaker than that of 0.735 wt % saline (exhibiting a salty taste-enhancing effect of less than 5%) or being unable to be evaluated because of a bitter taste or the like.

Table 1 and Table 2 show the results.

TABLE 1

| Synthesis Example | Structural formula | Name | Salty taste-enhancing effect | Foreign taste and foreign odor |
|---|---|---|---|---|
| 1 | 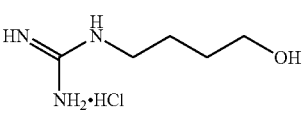 | 4-Guanidino-1-butanol hydrochloride | ++++ | Almost no foreign taste and foreign odor were sensed. |
| 2 | 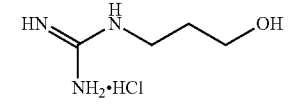 | 3-Guanidino-1-propanol hydrochloride | ++++ | Almost no foreign taste and foreign odor were sensed. |
| 3 | 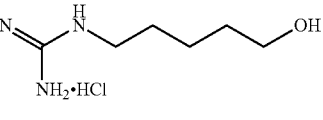 | 5-Guanidino-1-pentanol hydrochloride | ++++ | Almost no foreign taste and foreign odor were sensed. |
| 4 | 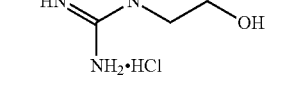 | 2-Guanidinoethanol hydrochloride | +++ | Almost no foreign taste and foreign odor were sensed. |
| 5 | 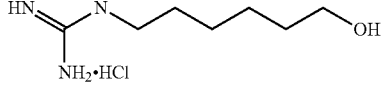 | 6-Guanidino-1-hexanol hydrochloride | ++ | A bitter taste was sensed. |
| 6 | 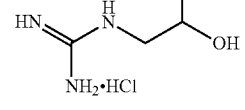 | 1-Guanidino-2-propanol hydrochloride | ++ | A slight foreign taste was sensed. |
| 7 | 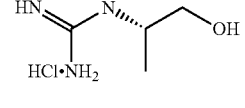 | 2-Guanidino-1-propanol hydrochloride | + | A bitter taste was sensed. |
| 8 | 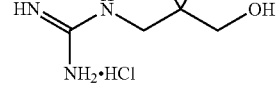 | 3-Guanidino-2,2-dimethyl-1-propanol hydrochloride | ++ | Almost no foreign taste and foreign odor were sensed. |
| 9 | 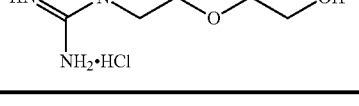 | 2-(2-Guanidinoethoxy)ethanol hydrochloride | ++ | Almost no foreign taste and foreign odor were sensed. |

TABLE 2

| Synthesis Example | Structural formula | Name | Salty taste-enhancing effect | Foreign taste and foreign odor |
|---|---|---|---|---|
| 10 | 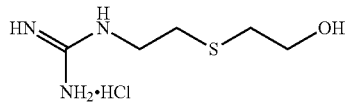 | 2-(2-Guanidinoethylthio)ethanol hydrochloride | + | A bitter taste was sensed. |

TABLE 2-continued

| Synthesis Example | Structural formula | Name | Salty taste-enhancing effect | Foreign taste and foreign odor |
|---|---|---|---|---|
| 11 | (R)-3-Guanidino-1,2-propanediol structure with NH₂·HCl | (R)-3-Guanidino-1,2-propanediol hydrochloride | ++ | Almost no foreign taste and foreign odor were sensed. |
| 12 | 1-Guanidinopropane structure with NH₂·HCl | 1-Guanidinopropane hydrochloride | ++ | Almost no foreign taste and foreign odor were sensed. |
| 14 | 3-Guanidino-1-propanol structure ·H₂SO₄ (bis) | 3-Guanidino-1-propanol sulfate | ++++ | A bitter taste was sensed. |
| — | Guanidine structure with NH₂·HCl | Guanidine hydrochloride | +++ | Almost no foreign taste and foreign odor were sensed. |
| — | β-Guanidinopropanoic acid structure | β-Guanidinopropanoic acid | ++ | Almost no foreign taste and foreign odor were sensed. |
| — | γ-Guanidinobutyric acid structure | γ-Guanidinobutyric acid | ++ | Almost no foreign taste and foreign odor were sensed. |
| — | 6-Guanidinocaproic acid structure | 6-Guanidinocaproic acid | + | Almost no foreign taste and foreign odor were sensed. |

The results showed that the salty taste-enhancing agent of the present invention had a salty taste-enhancing action.

Example 2

Sensory Evaluation

3-Guanidino-1-propanol hydrochloride obtained in Synthesis Example 2 was evaluated for its relationship between an addition concentration and a salty taste-enhancing action.

3-Guanidino-1-propanol hydrochloride and sodium chloride (salt) were dissolved in distilled water to prepare an aqueous solution containing 1.5 ppm (0.00015 wt %), 15 ppm (0.0015 wt %), 150 ppm (0.015 wt %), or 1,500 ppm (0.15 wt %) of 3-guanidino-1-propanol hydrochloride and 0.700 wt % of sodium chloride, which was used as an evaluation solution. In addition, solutions containing 0.700 wt %, 0.735 wt %, 0.770 wt %, 0.805 wt %, and 0.840 wt % of sodium chloride were used as comparative objects.

Each evaluation sample was subjected to sensory evaluation based on the following criteria.

++++: exhibiting a salty taste equal to or stronger than that of 0.840 wt % saline (exhibiting a salty taste-enhancing effect of 20% or more);

+++: exhibiting a salty taste equal to or stronger than that of 0.805 wt % saline (exhibiting a salty taste-enhancing effect of 15% or more);

++: exhibiting a salty taste equal to or stronger than that of 0.770 wt % saline (exhibiting a salty taste-enhancing effect of 10% or more);

+: exhibiting a salty taste equal to or stronger than that of 0.735 wt % saline (exhibiting a salty taste-enhancing effect of 5% or more); and ±: exhibiting a salty taste weaker than that of 0.735 wt % saline (exhibiting a salty taste-enhancing effect of less than 5%).

Table 3 shows the results.

TABLE 3

| Addition concentration | Salty taste-enhancing effect |
|---|---|
| 1.5 ppm (0.00015%) | ± |
| 15 ppm (0.0015%) | + |
| 150 ppm (0.015%) | ++ |
| 1,500 ppm (0.15%) | ++++ |

The results revealed that 3-guanidino-1-propanol hydrochloride exhibited a salty taste-enhancing action at an addition concentration of 15 ppm or more, and its effect was concentration-dependent.

Example 3

Evaluation for Salty Taste-Enhancing Effect in Food and Beverage

3-Guanidino-1-propanol hydrochloride obtained in Synthesis Example 2 was evaluated for its salty taste-enhancing effect in a food and beverage.

Raw materials were blended according to Table 4 shown below (powder soup for noodles). The blended raw materials were dissolved in 1,000 ml of hot water to afford foods and beverages with a control formulation and a reduced-salt formulation (noodle soup for instant noodles). The salt content concentrations in terms of sodium (Na) of the control formulation soup and the reduced-salt formulation soup are 1.02% and 0.76%, respectively. Accordingly, the reduced-salt formulation has a salt content reduced by 25% as compared to the control formulation.

TABLE 4

| | Per L (g) | |
|---|---|---|
| | Control formulation | Reduced-salt formulation |
| Purified salt | 7.93 | 5.36 |
| Sugar | 10.13 | 10.13 |
| Sodium glutamate | 0.66 | 0.66 |
| Nucleic acid seasoning | 0.44 | 0.44 |
| Acidulant | 0.13 | 0.13 |
| Flavor | 0.13 | 0.13 |
| Powder caramel | 0.66 | 0.66 |
| Hydrolyzed protein | 0.77 | 0.77 |
| Vegetable extract | 0.88 | 0.88 |
| Dried bonito/bonito extract | 5.07 | 5.07 |
| Powder soy sauce | 2.09 | 2.09 |
| Shichimi togarashi | 0.15 | 0.15 |
| Total | 29.05 | 26.48 |
| Salt content concentration (in terms of Na) | 1.02% | 0.76% |

3-Guanidino-1-propanol hydrochloride obtained in Synthesis Example 2 was added at concentrations of 0.1 wt %, 0.15 wt %, and 0.20 wt % to the reduced-salt formulation soup to prepare Samples 1 to 3, respectively. Samples 1 to 3 were subjected to a sensory test based on a paired comparison with each of the control formulation soup and the reduced-salt formulation soup.

Table 5 shows the results of the sensory test.

TABLE 5

| | 3-Guanidino-1-propanol hydrochloride (wt %) | Sensory evaluation result |
|---|---|---|
| Control formulation | 0 | |
| Reduced-salt formulation | 0 | The whole taste including the salty taste was light as compared to the control formulation. |
| Sample 1 | 0.1 | The salty taste was markedly increased as compared to the reduced-salt formulation, but was weak as compared to the control formulation. |
| Sample 2 | 0.15 | The salty taste was slightly weak as compared to the control formulation. |
| Sample 3 | 0.2 | There was almost no difference from the control formulation in taste and flavor including the salty taste. |

As shown in Table 5, it was found that the salty taste-enhancing effect was improved depending on the concentration of 3-guanidino-1-propanol hydrochloride, and its addition at 0.2 wt % exhibited a salty taste-enhancing effect of 25% in the noodle soup for instant noodles. In addition, when 3-guanidino-1-propanol hydrochloride was added at 0.2 wt %, no remarkable foreign taste and foreign odor were sensed.

The results revealed that 3-guanidino-1-propanol hydrochloride at an addition concentration of 0.2 wt % exhibited a salty taste-enhancing effect of at least 25% in a food and beverage as well.

The invention claimed is:

1. A food or beverage, comprising a sodium chloride content of about 0.2 to 2.0 wt % and 15 ppm or more of a compound represented by the following general formula (7) or a salt thereof:

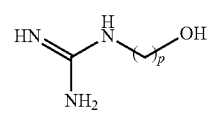

(7)

where p represents an integer of from 3 to 5, said food or beverage having an enhanced salt taste of greater than 5% due to said compound, over the same food or beverage without the compound.

2. A salty taste-enhancing method for a food or beverage, comprising a step of adding a compound represented by the following general formula (7) or a salt thereof:

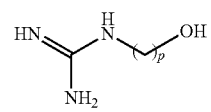

(7)

where p represents an integer of from 3 to 5, to a food or beverage containing a sodium chloride content of about 0.2 to 2.0 wt %, and to a content of 15 ppm or more, thereby enhancing, by an amount greater than 5%, the salty taste of the food or beverage, over the same food or beverage without the compound.

3. The food or beverage according to claim 1, wherein sodium chloride content of the food or beverage is about 0.5 to 1.5 wt %.

4. The method according to claim 2, wherein sodium chloride content of the food or beverage is about 0.5 to 1.5 wt %.

* * * * *

UNITED STATES PATENT AND TRADEMARK OFFICE
CERTIFICATE OF CORRECTION

PATENT NO. : 12,122,736 B2
APPLICATION NO. : 14/436449
DATED : October 22, 2024
INVENTOR(S) : Sakurai et al.

It is certified that error appears in the above-identified patent and that said Letters Patent is hereby corrected as shown below:

On the Title Page

Item [73], delete "Nissan Foods Holdings CO., LTD." and insert --Nissin Foods Holdings CO., LTD.--

Signed and Sealed this
Nineteenth Day of November, 2024

Katherine Kelly Vidal
*Director of the United States Patent and Trademark Office*